(12) United States Patent
Fleury et al.

(10) Patent No.: US 10,456,011 B2
(45) Date of Patent: Oct. 29, 2019

(54) METHODS AND SYSTEMS FOR ATTACHING MEDICAL DEVICE SECTIONS

(71) Applicant: Boston Scientific Scimed, Inc., Maple Grove, MN (US)

(72) Inventors: Sean P. Fleury, Brighton, MA (US); Gary S. Kappel, Acton, MA (US); Norman C. May, Northborough, MA (US); Dane T. Seddon, Boston, MA (US); Mark D. Wood, Shrewsbury, MA (US); Peter L. Dayton, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 416 days.

(21) Appl. No.: 15/003,415

(22) Filed: Jan. 21, 2016

(65) Prior Publication Data

US 2016/0135665 A1 May 19, 2016

Related U.S. Application Data

(63) Continuation of application No. 13/754,560, filed on Jan. 30, 2013, now Pat. No. 9,272,128.
(Continued)

(51) Int. Cl.
*A61B 1/00* (2006.01)
*A61M 39/12* (2006.01)
(Continued)

(52) U.S. Cl.
CPC ........ *A61B 1/00071* (2013.01); *A61B 1/0055* (2013.01); *A61B 1/00128* (2013.01);
(Continued)

(58) Field of Classification Search
CPC .... A61B 17/00234; A61B 2017/00292; A61B 2017/00003; A61B 2017/00305;
(Continued)

(56) References Cited

U.S. PATENT DOCUMENTS 6,742,681 B1 * 6/2004 Yang .................... B65D 47/247
                                                            220/703
7,083,629 B2 * 8/2006 Weller ............... A61B 17/0482
                                                            606/151
(Continued)

FOREIGN PATENT DOCUMENTS

EP        1 563 784 A1    8/2005
EP        2 052 672 A1    4/2009
(Continued)

OTHER PUBLICATIONS

Communication Relating to the Results of the Partial International Search from corresponding international application PCT/US2013/023883, dated May 17, 2013.

*Primary Examiner* — Ahmed M Farah
(74) *Attorney, Agent, or Firm* — Bookoff McAndrews, PLLC

(57) ABSTRACT

Embodiments of the disclosure include methods and systems for attaching an articulation section. In an embodiment, a medical instrument includes a first tubular member including a first end. The medical instrument also includes a second tubular member including a first end. The second tubular member includes a plurality of layers including an inner layer and a first layer including a fluorinated material. The inner layer includes a first section disposed under the first layer and a second section extending out from under the first layer. A portion of the first tubular member overlaps and is bonded to at least a portion of the second section of the inner layer of the second tubular member.

6 Claims, 28 Drawing Sheets

Related U.S. Application Data

(60) Provisional application No. 61/593,121, filed on Jan. 31, 2012, provisional application No. 61/592,995, filed on Jan. 31, 2012.

(51) Int. Cl.
*A61M 25/00* (2006.01)
*A61B 1/005* (2006.01)
*A61B 17/29* (2006.01)
*A61B 17/00* (2006.01)

(52) U.S. Cl.
CPC ......... *A61B 17/29* (2013.01); *A61M 25/0043* (2013.01); *A61M 39/12* (2013.01); *A61B 2017/0034* (2013.01); *A61B 2017/00314* (2013.01); *A61B 2017/00323* (2013.01); *A61B 2017/00464* (2013.01); *A61B 2017/00473* (2013.01); *A61B 2017/00477* (2013.01); *A61B 2017/2905* (2013.01)

(58) Field of Classification Search
CPC ........... A61B 2017/00314; A61B 2017/00318; A61B 2017/0034; A61B 2017/00367; A61B 2017/00477; A61B 1/00071; A61B 1/0008; A61B 1/00112; A61B 1/00121; A61B 1/00128; A61B 1/00131; A61B 1/00133
USPC .... 606/1, 130; 600/101, 104, 114, 121, 129, 600/130, 139
See application file for complete search history.

(56) References Cited

U.S. PATENT DOCUMENTS

| | | | |
|---|---|---|---|
| 7,600,657 B2 * | 10/2009 | Wang | A45F 3/16 222/175 |
| 9,033,975 B2 * | 5/2015 | Seddon | A61B 18/1482 606/41 |
| 9,463,063 B2 * | 10/2016 | Seddon | A61B 18/1482 |
| 2002/0022833 A1 * | 2/2002 | Maguire | A61B 17/2202 606/27 |
| 2007/0156115 A1 | 7/2007 | Hosoi et al. | |
| 2008/0188868 A1 | 8/2008 | Weitzner et al. | |
| 2008/0243106 A1 * | 10/2008 | Coe | A61B 17/00234 606/1 |
| 2010/0198231 A1 | 8/2010 | Scott | |
| 2011/0112434 A1 * | 5/2011 | Ghabrial | A61B 1/00135 600/564 |
| 2012/0197241 A1 | 8/2012 | Golden et al. | |
| 2013/0197491 A1 | 8/2013 | Golden et al. | |
| 2013/0240545 A1 * | 9/2013 | O'Sullivan | A47G 19/2222 220/710 |

FOREIGN PATENT DOCUMENTS

| | | |
|---|---|---|
| EP | 2 108 301 A1 | 10/2009 |
| WO | WO 2004/096335 A1 | 11/2004 |
| WO | WO 2012/106186 A1 | 8/2012 |
| WO | WO 2013/116499 A1 | 8/2013 |

* cited by examiner

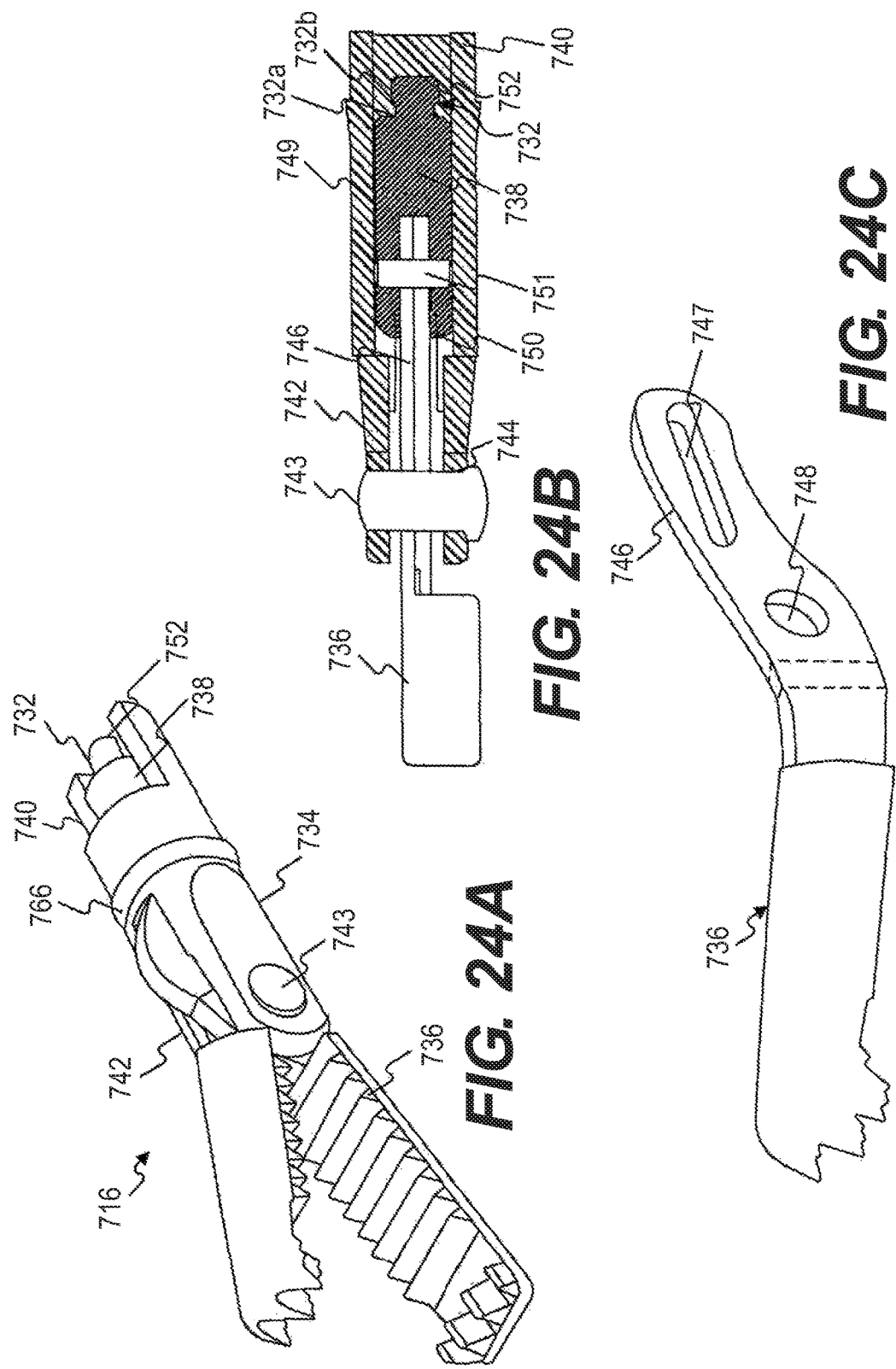

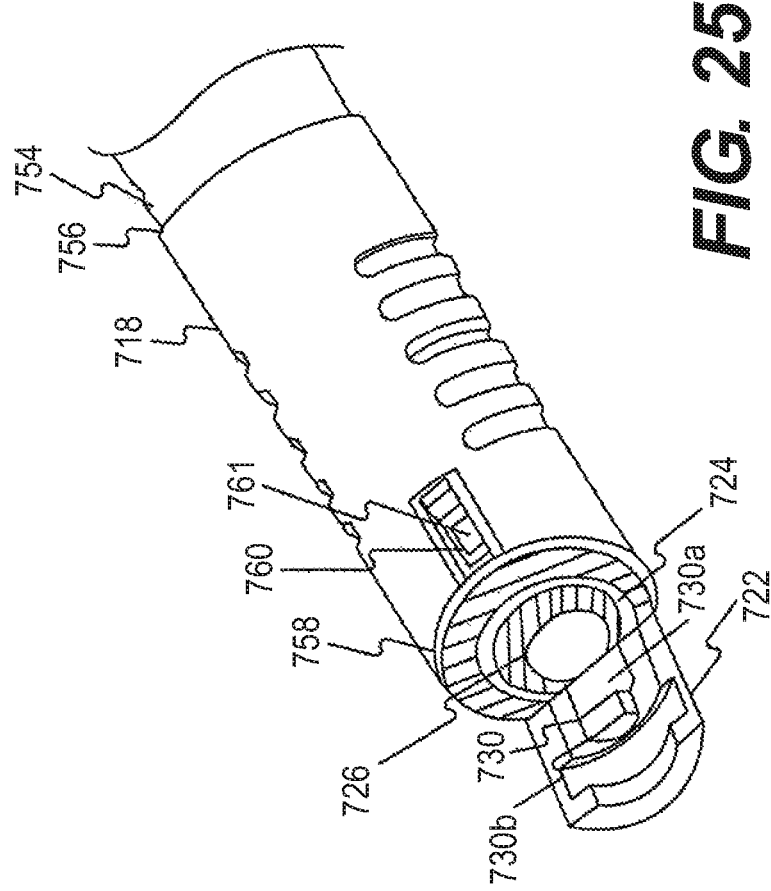

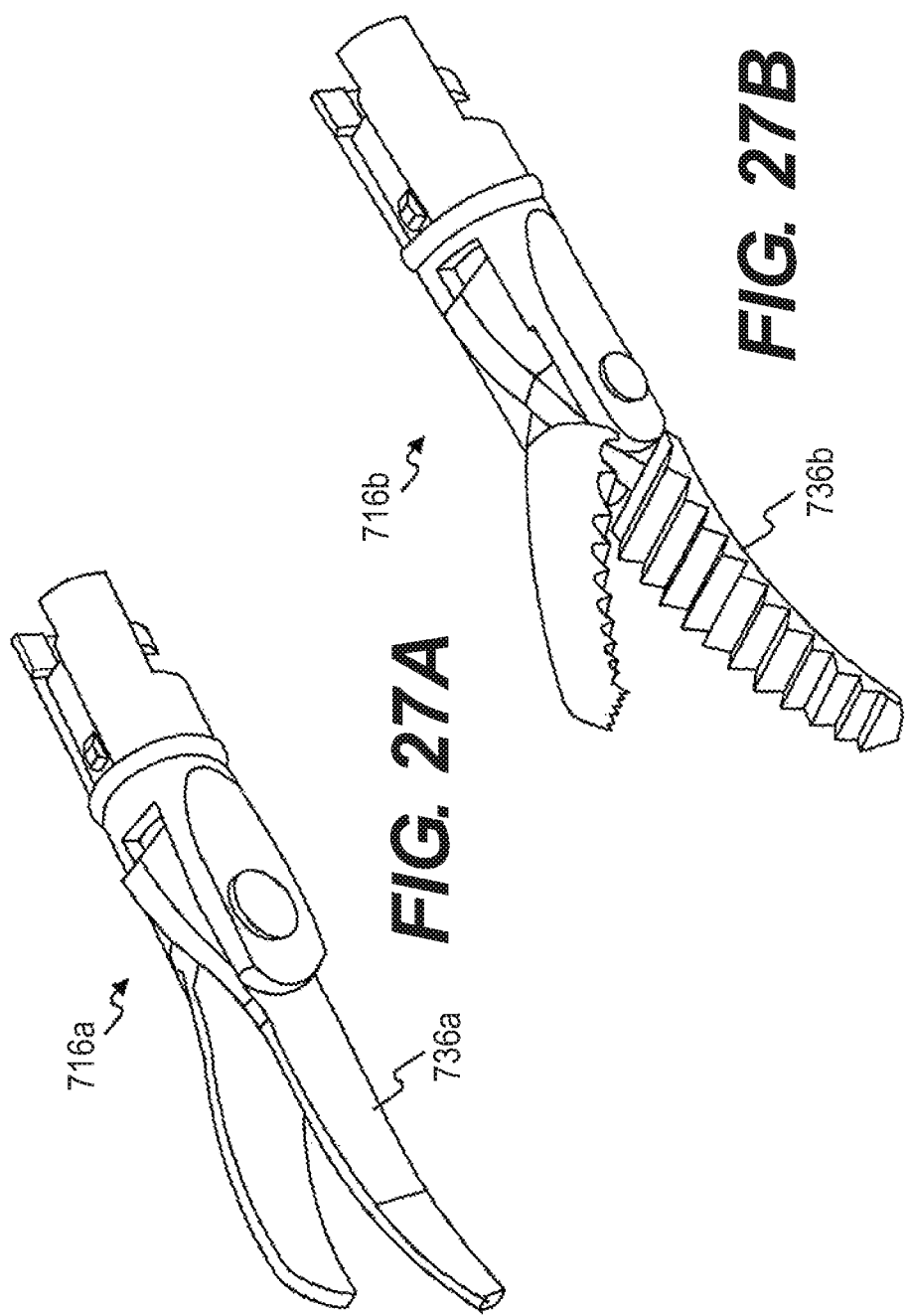

METHODS AND SYSTEMS FOR ATTACHING MEDICAL DEVICE SECTIONS

This application is a Continuation of U.S. application Ser. No. 13/754,560, filed Jan. 30, 2013, now U.S. Pat. No. 9,272,128, which claims the benefit of U.S. Provisional Application No. 61/592,995, filed Jan. 31, 2012, and U.S. Provisional Application No. 61/593,121, filed Jan. 31, 2012, the disclosures of all of which are incorporated by reference herein in their entireties.

FIELD

The present disclosure relates to a medical device with an articulation section, and more particularly to methods and systems for attaching medical device sections.

BACKGROUND

Articulated medical devices provide access to sites within a patient's body that are difficult to reach using rigid non-articulating devices. For example, articulated endoscopes provide direct access to internal organs and articulated catheters provide access to tortuous vascular structures.

Articulated medical devices have traditionally been flexible to provide easy manipulation, e.g., to navigate through the lower gastro-intestinal tract. However, it may be difficult to attach an articulation section to the shaft of the medical device if the articulation section and the shaft are formed with flexible materials.

The methods and systems for attaching an articulation section described herein overcome these and other limitations of the prior art. The attachment systems and methods of the present disclosure are broadly applicable to various medical devices and other devices requiring articulation. For example, borescopes use articulation to access difficult-to-reach locations within engines or other industrial devices.

Further, a wide variety of medical devices can be employed to assist in performing endoscopic, laparoscopic, percutaneous, or transluminal procedures. These devices include operable end-effectors such as, for example, cutting blades, forceps, graspers, dissectors, scissors, biopsy forceps, or other types of tools.

It is sometimes necessary to utilize one or more end-effectors during the course of a procedure. In such instances, it may be both economical and efficient to replace the end-effector on the device shaft, instead of replacing the device. It may also be desirable to provide a reusable device handle and shaft. Such arrangements may reduce the overall cost of the device, and allow for hospital inventory control, as a stock device shaft may be provided and any one of multiple end-effectors may be interchangeably used with the device shaft when necessary. As such, there is a need for a mechanism that permits a quick connection and disconnection of an end-effector from a device shaft.

SUMMARY

In accordance with an embodiment, a medical instrument includes a first tubular member including a first end. The medical instrument also includes a second tubular member including a first end. The second tubular member includes a plurality of layers including an inner layer and a first layer including a fluorinated material. The inner layer includes a first section disposed under the first layer and a second section extending out from under the first layer. A portion of the first tubular member overlaps and is bonded to at least a portion of the second section of the inner layer of the second tubular member.

In accordance with another embodiment, an adapter for an articulation section includes a body configured to receive a bend portion of a first articulation elongate member. The body includes a first end configured to be attached to an end effector and a second end configured to be coupled to an articulation link of the articulation section. The body includes a first cavity at least partially defined by a first ledge. The first ledge includes a bend configured to support the bend portion of the first articulation elongate member. The body also includes at least one channel extending from the first cavity toward the second end of the body. The at least one channel is configured to receive portions of the first articulation elongate member that are attached to the bend portion. The adapter also includes a first anchoring member configured to fixedly attach the bend portion of the first articulation elongate member to the body.

In accordance with yet another embodiment, an adapter for an articulation section includes a body. The body includes a first end configured to be coupled to an articulation link of the articulation section and a second end configured to be received in an end of a tubular member. The body also includes a cavity disposed at the first end, and the cavity is configured to receive a protrusion in the articulation link. The body also includes a flange disposed at the first end, and the flange includes a plurality of first channels configured to align with corresponding first channels in the tubular member and the articulation link. The body also includes a tubular portion disposed at the second end and configured to be received in one of a second channel of the tubular member.

In accordance with an embodiment, medical devices have a separable end-effector and a securing member.

In accordance with another embodiment, a medical device may include an elongate shaft having a proximal end and a distal portion. The medical device may further include an end-effector assembly configured to be releasably connected to the distal portion of the shaft. The medical device may further include a connection portion, wherein the distal portion of the shaft and a portion of the end-effector assembly form the connection portion. The medical device may also include a securing member. The securing member may be movable between a first position away from the connection portion and a second position. In the second position, the securing member may be disposed about the connection portion and configured to connect the end-effector assembly to the distal portion of shaft.

In accordance with another embodiment, a medical device may include one or more of the following features: wherein, in the first position, the securing member is disposed proximally of the distal portion of the shaft; wherein the securing member has a proximal end that is closer to the distal portion of the shaft than the proximal end of the shaft; wherein the end-effector assembly includes a clevis having a proximal portion, and wherein the proximal portion of the clevis and the distal portion of the shaft form the connection portion; wherein the securing member is configured to move relative to the distal portion of the shaft and the end-effector assembly when the proximal portion and the distal portion form the connection portion; wherein the securing member includes a retainer, and the proximal portion includes a protrusion, the retainer being configured to receive the protrusion when the securing member is in the second position; wherein the clevis includes a rim, and wherein a distal end of the securing member abuts the rim in the second position.

In accordance with another embodiment, a medical device may include an elongate shaft having a proximal end, a distal portion, and a lumen extending distally from the proximal end to the distal portion. Medical device may also include an elongate member extending through the lumen, the elongate member having a first fitting. An end-effector assembly may include an end-effector and an actuator. The actuator may be connected to the end-effector and may also have a second fitting. A securing member may be configured to connect the end-effector assembly to the distal portion of the shaft when the first fitting is aligned with the second fitting.

In accordance with another embodiment, the medical device may include one or more of the following additional features: wherein the end-effector assembly further includes a clevis having a proximal portion, and wherein the proximal portion and the distal portion form a connection portion when the first fitting is aligned with the second fitting; wherein the securing member is configured to move relative to the distal portion of the shaft and the end-effector assembly when the proximal portion and the distal portion form the connection portion; wherein the securing member includes a retainer configured to receive a protrusion on the proximal portion of the clevis; wherein the actuator and the elongate member are adapted to move relative to the lumen of the shaft, when the protrusion is received in the retainer; wherein the securing member is disposed on an exterior of the shaft; and wherein the securing member has a proximal end that is closer to the distal portion of the shaft than the proximal end of the shaft.

In accordance with another embodiment, a method of assembling a medical device may include aligning an end-effector assembly with a distal portion of a shaft; and engaging a securing member with the end-effector assembly to secure the end-effector assembly to the distal portion of the shaft.

In accordance with another embodiment, a method may include one or more of the following features: wherein the end-effector assembly includes a clevis having a proximal portion, and wherein aligning the end-effector assembly with the distal portion of the shaft includes aligning the proximal portion of the clevis and the distal portion of the shaft to form a connection portion; wherein engaging the securing member includes moving the securing member relative to the distal portion of the shaft and the end-effector assembly when the proximal portion of the clevis and the distal portion of the shaft form the connection portion; wherein the securing member includes a retainer, and the method further including coupling the end-effector assembly to the distal end of the shaft by receiving a protrusion on the proximal portion of the clevis in the retainer; further including disengaging the securing member from the end-effector assembly by moving the securing member relative to the distal portion of the shaft and the end-effector assembly to decouple the end-effector assembly from the distal portion of the shaft; and further including limiting movement of the securing member relative to the end-effector assembly.

Additional objects and advantages of the disclosure will be set forth in part in the description which follows, and in part will be obvious from the description, or may be learned by practice of the disclosure. The objects and advantages of the disclosure will be realized and attained by means of the elements and combinations particularly pointed out below.

It is to be understood that both the foregoing general description and the following detailed description are exemplary and explanatory only and are not restrictive of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

FIG. 24A is a perspective view of an end-effector assembly of the medical device of FIG. 22, according to an exemplary embodiment of the disclosure;

FIG. 24B is a longitudinal cross-section of a clevis of the end-effector assembly of FIG. 24A, according to an exemplary embodiment of the disclosure;

FIG. 24C is perspective view of an end-effector, according to an exemplary embodiment of the disclosure;

FIG. 25 is a partial perspective view of a shaft of the medical device of FIG. 22 and a securing member disposed on an exterior of the shaft, according to an exemplary embodiment of the disclosure;

FIGS. 27A-B illustrate alternative non-limiting end-effector assemblies of the medical device of FIG. 22, according to exemplary embodiments of the disclosure.

DESCRIPTION OF THE EMBODIMENTS

Reference will now be made in detail to exemplary embodiments of the disclosure, examples of which are illustrated in the accompanying drawings. Wherever possible, the same reference numbers will be used throughout the drawings to refer to the same or like parts. Also, any aspect set forth in any embodiment may be used with any other embodiment set forth herein.

Figure 1:
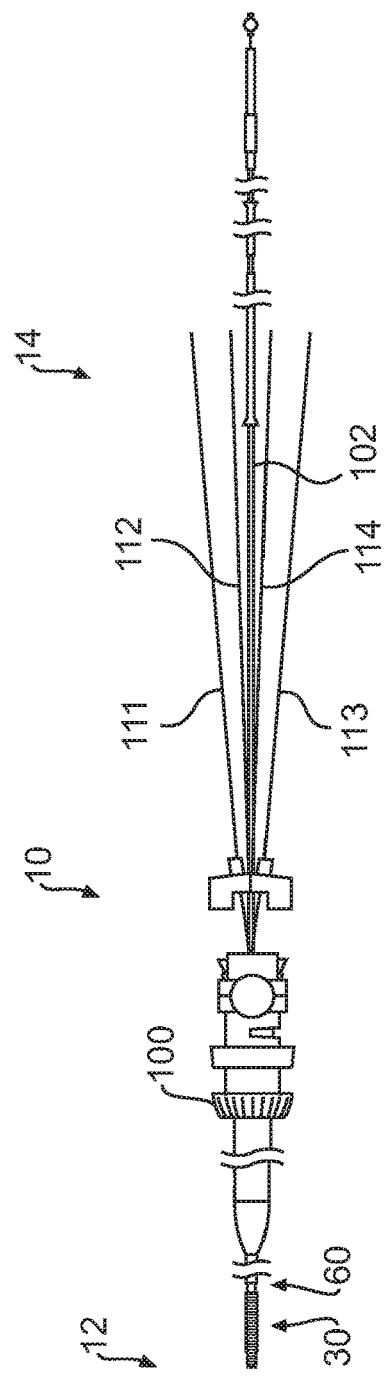
FIG. 1 is a side view of an instrument assembly, according to an exemplary embodiment.
Figure 2:
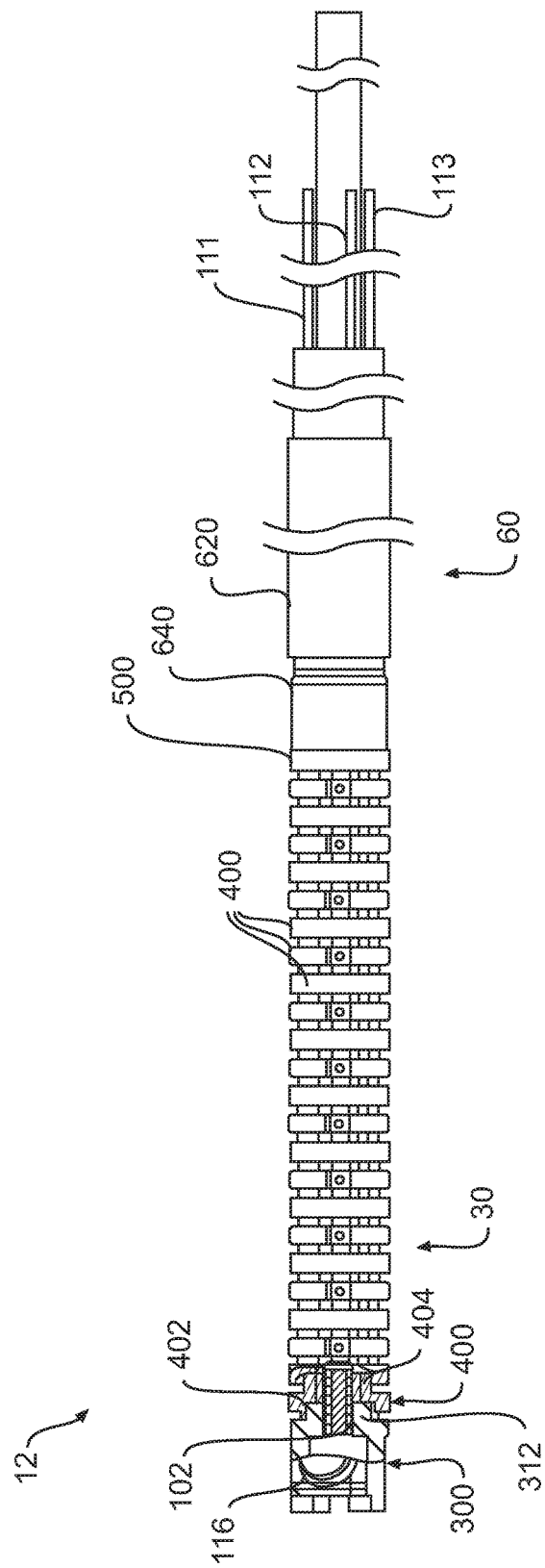
FIG. 2 is a cross-sectional side view of a distal end of the instrument assembly of FIG. 1.

FIGS. 1 and 2 show an instrument assembly 10 according to an exemplary embodiment. The instrument assembly 10 may be used for any therapeutic or diagnostic endoscopic procedure and the steps thereof. The phrase "endoscopic procedure" is broadly used to indicate any medical procedure that may be performed by inserting an endoscope, guide tube, catheter, or any other medical device into the body through any anatomic opening or incision. The instrument assembly 10 may be used for performing surgery at a relative distance from a surgeon. The instrument assembly 10 may be adapted for trans-oral, trans-anal, trans-vaginal, trans-urethral, trans-nasal, transluminal, laparoscopic, thoracoscopic, orthopedic, through the ear, and/or percutaneous access. The components of the instrument assembly 10 described below may be made of any suitable material capable of being inserted into the body, e.g., a suitable biocompatible material.

The terms "proximal" and "distal" are used herein to refer to the relative positions of the components of the exemplary instrument assembly 10. When used herein, "proximal" refers to a position relatively closer to the surgeon using the instrument assembly 10. In contrast, "distal" refers to a position relatively further away from the surgeon using the instrument assembly 10 or closer to a surgical site located within the patient's body.

In addition, while the discussion of systems and methods below may generally refer to "surgical instruments," "surgery," or a "surgical site" for convenience, the described systems and their methods of use are not limited to tissue resection and/or repair. In particular, the described systems may be used for inspection and diagnosis in addition, or as an alternative, to surgical treatment. The treatment is not limited to any particular treatment. Various other exemplary treatment devices and methods are referred to herein. Moreover, the systems described herein may perform non-medical applications such as in the inspection and/or repair of machinery.

The instrument assembly 10 may be configured to be advanced through any anatomical opening and/or body lumen. For example, the instrument assembly 10 may be used in natural orifice transluminal endoscopic surgery (NOTES) procedures or single incision laparoscopic surgical (SILS) procedures. Accordingly, the instrument assembly 10 may be shaped and sized for placement into a patient via a body cavity or an incision.

The instrument assembly 10 may have a distal end 12 and a proximal end 14. In order from the distal end 12 to the proximal end 14, the instrument assembly 10 may include an end effector 20 (FIGS. 3 and 4), an articulation section 30, and an instrument shaft section 60.

The proximal end 14 of the instrument assembly 10 may include various mechanisms for allowing the user to control the distal end 12 of the instrument assembly 10. The proximal end 14 may include one or more knobs, handles, control members, or other devices configured to move the distal end 12 relative to the proximal end 14. For example, a knob 100 may control the movement of the distal end 12 along a distal direction and proximal direction, or rotationally relative to the proximal end 14. Some exemplary components for controlling movement of the distal end of an instrument assembly are disclosed, for example, in U.S. Patent Application Publication No. 2008/0188868, entitled "Direct Drive Endoscopy Systems and Methods" and the U.S. Provisional Application No. 61/593,209, both of which are hereby incorporated by reference in their entirety.

One or more actuation control members 102 (e.g., with or without one or more grippers) may control the actuation of the end effector 20. The control member 102 can include a wire, a cable, a ribbon, or similar elongate structure. In the exemplary embodiment shown in FIG. 1, one actuator control member 102 is provided. For example, the actuator control member 102 may allow the operator to actuate the end effector 20 when the actuator control member 102 is pulled in the proximal direction or pushed in the distal direction. The actuator control member 102 may also be configured to transmit an electrical current to the distal end 12.

One or more articulation control members may control the articulation of the articulation section 30 as described below. For example, the articulation control members may be braided wire. In the exemplary embodiment shown in FIG. 1, the instrument assembly 10 may include two articulation control members. Each articulation control member may extend from the proximal end 14 of the instrument assembly 10 to a distal adapter 300 (described below) of the articulation section 30, where the articulation control member bends and extends back to the proximal end 14 of the instrument assembly 10. Thus, one articulation control member may include two articulation control member portions 111 and 112 and a bend portion 116 (FIGS. 2, 5, and 8-10) connecting the portions 111 and 112. The other articulation control member may also include two articulation control member portions 113 and 114 and another bend portion 116 connecting the portions 113 and 114. The four articulation control member portions 111, 112, 113, and 114 may control articulation of the articulation section 30 in four directions (e.g., right, up, left, and down, respectively). For example, when the operator pulls the first articulation control member portion 111 or 113 in the proximal direction, the articulation section 30 may be articulated in the right or left direction, respectively. When the operator pulls the first articulation control member portion 112 or 114 in the proximal direction, the articulation section 30 may be articulated in the up or down direction, respectively. Alternatively, the instrument assembly 10 may include one articulation control member, or more than two articulation control members, depending on a desired range of movement of the instrument assembly 10.

Figure 3:
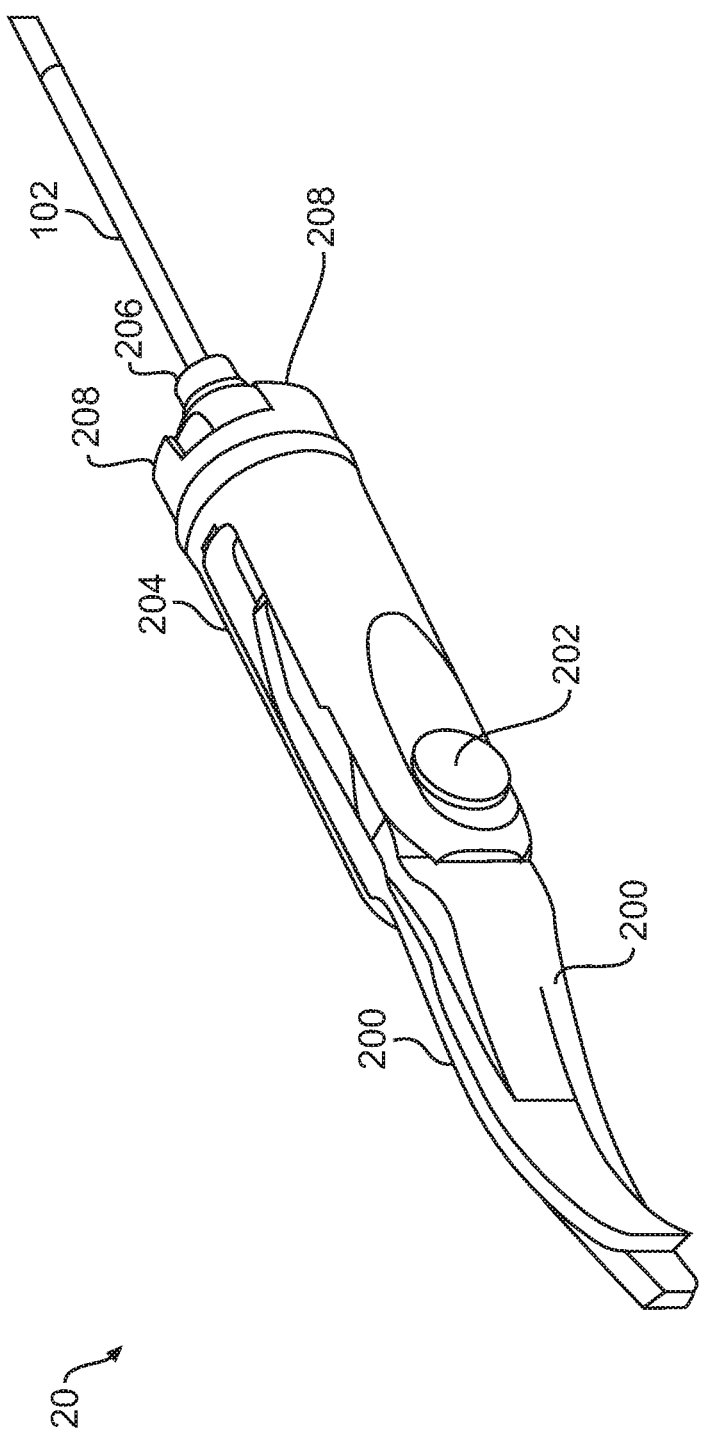
FIG. 3 is a perspective view of an end effector in a first position, according to an exemplary embodiment.
Figure 4:
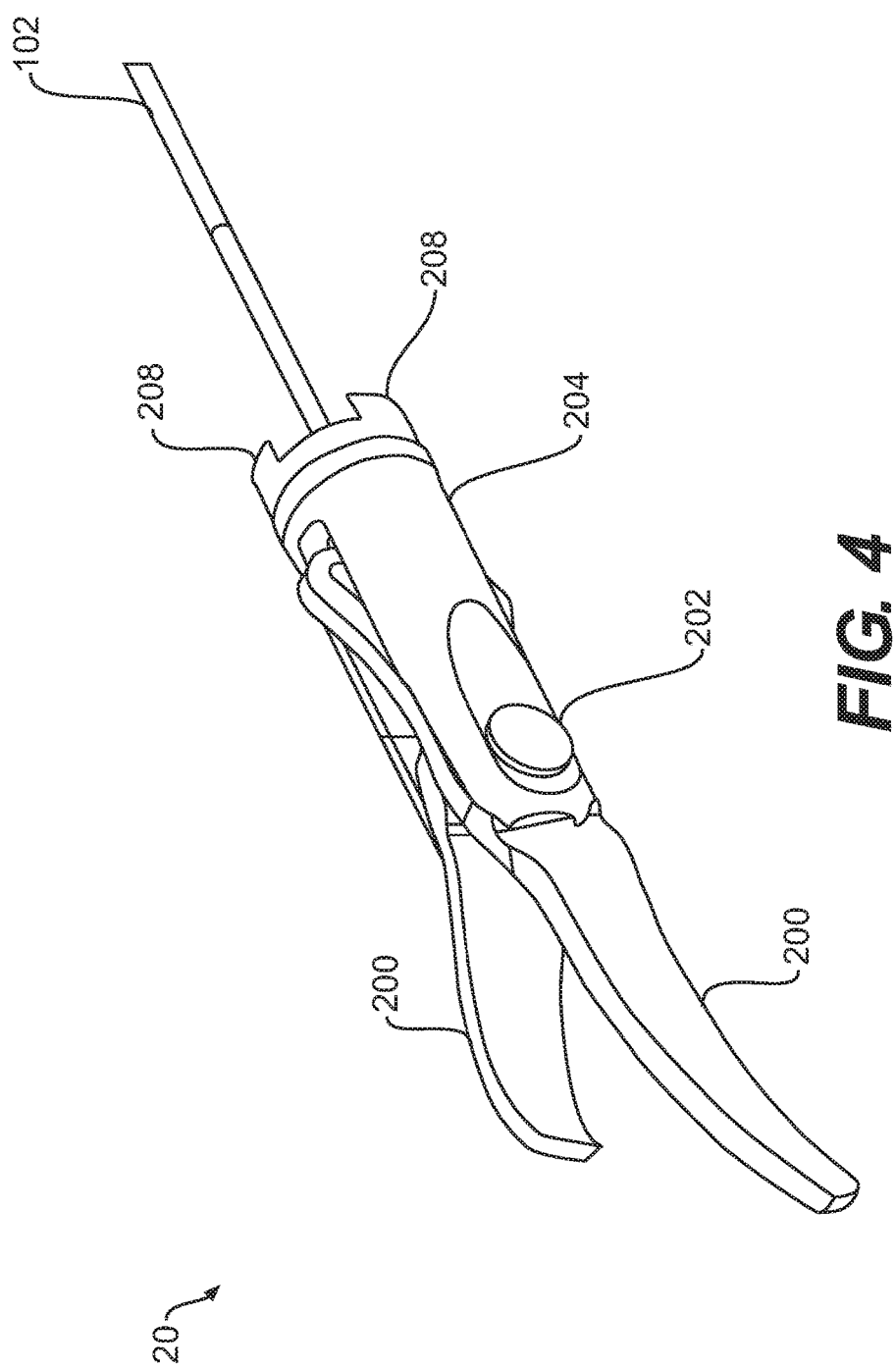
FIG. 4 is a perspective view of the end effector of FIG. 3 in a second position.

FIGS. 3 and 4 show the end effector 20 in the form of a pair of scissors according to an exemplary embodiment. Alternatively, the end effector 20 may include a grasper, a hook, an ablation device, or other type of surgical or electrosurgical instrument configured to operate with, or include, insufflation, irrigation, suction, imaging, or other devices used in endoscopic, laparoscopic, or other surgical procedures. In the exemplary embodiment, the end effector 20 may be formed of a rigid material, such as stainless steel.

The distal end of the end effector 20 of the exemplary embodiment may include scissor blade portions 200, which are pivotally attached by a pivot pin 202 to a clevis 204 at a proximal end of the end effector 20. The proximal end of the clevis 204 may be received in and attached to a distal end of the articulation section 30. The scissor blade portions 200 also pivotally attach to an actuator 206 slidably disposed in the clevis 204. A distal end of the actuator 206 may be pivotally attached to respective grooves (not shown) in the scissor blade portions 200 via a link pin (not shown). A proximal end of the actuator 206 may be attached (e.g., by welding) to the distal end of the actuation control member 102 that extends to the proximal end 14 of the instrument assembly 10 to allow the operator to control the actuation of the end effector 20. For example, FIG. 3 shows the actuator 206 in a normal position with the scissor blade portions 200 closed. In this position, when the operator pushes the actuation control member 102 in the distal direction, the actuator 206 may slide in the distal direction relative to the clevis 204, thereby causing the link pin to slide within the grooves in the scissor blade portions 200 and causing the scissor blade portions 200 to open. When the operator pulls back the actuation control member 102, the actuator 206 may slide in the proximal direction relative to the clevis 204, thereby causing the scissor blade portions 200 to close.

The proximal end of the clevis 204 may include one or more proximal protrusions 208 configured to be inserted into corresponding notches in the distal end of the articulation section 30 as described below. In the exemplary embodiment shown in FIGS. 3 and 4, the clevis 204 includes two proximal protrusions 208. The two proximal protrusions 208 may be disposed on opposite sides of the clevis 204 with respect to a longitudinal axis of the clevis 204 and the end effector 20. The shape of the proximal protrusions 208 may correspond to notches formed between corresponding distal protrusions 308 (FIGS. 5-10) as described below.

The end effector 20 may be connected to a distal adapter 300 at the distal end of the articulation section 30. The articulation section 30 may also include a series of articulation links 400 and a proximal adapter 500 (FIGS. 13, 15, 17, 19, and 21) for connecting to the instrument shaft section 60. Some exemplary configurations of articulation links and articulation sections are disclosed, for example, in U.S. Provisional Application No. 61/438,072 and U.S. patent application Ser. No. 13/360,018, both entitled "Articulation Joints for Torque Transmission," both of which are hereby incorporated by reference in their entirety.

Figure 5:
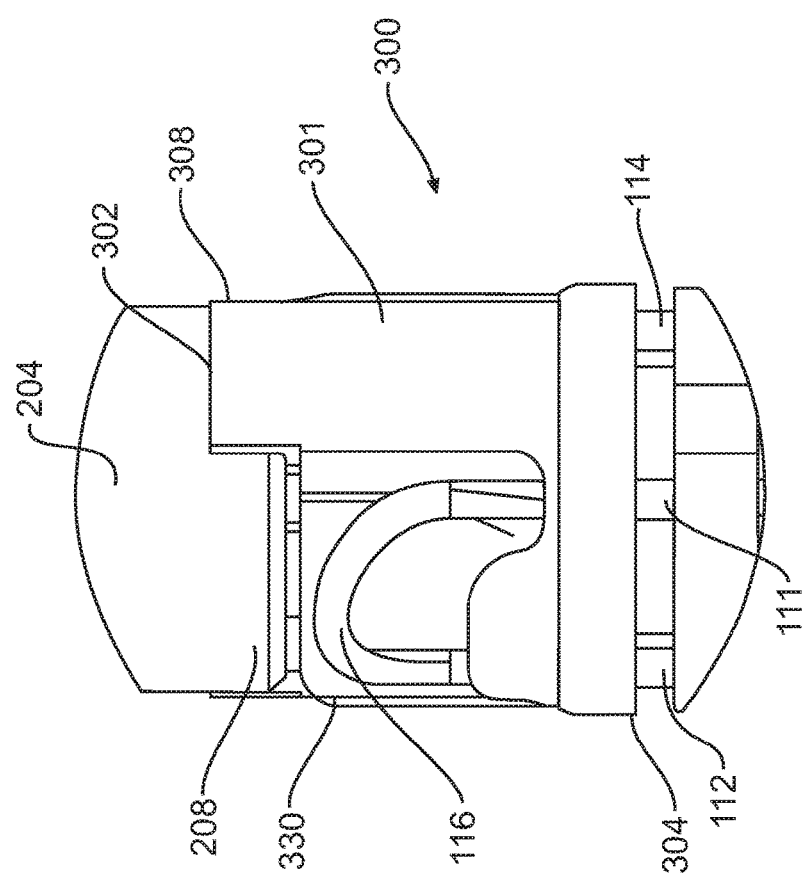
FIG. 5 is a side view of an end effector attached to a distal adapter of an articulation section, according to an exemplary embodiment.

FIG. 5 shows the proximal end of the clevis 204 of the end effector 20 attached to the distal adapter 300, according to an exemplary embodiment. The distal adapter 300 may include a body 301 and one or more anchoring members 330 that may fix the bend portions 116 of the articulation control members to the body 301. Each of the articulation control member portions 111, 112, 113, and 114 may extend in the proximal direction from the distal adapter 300.

Figure 6:
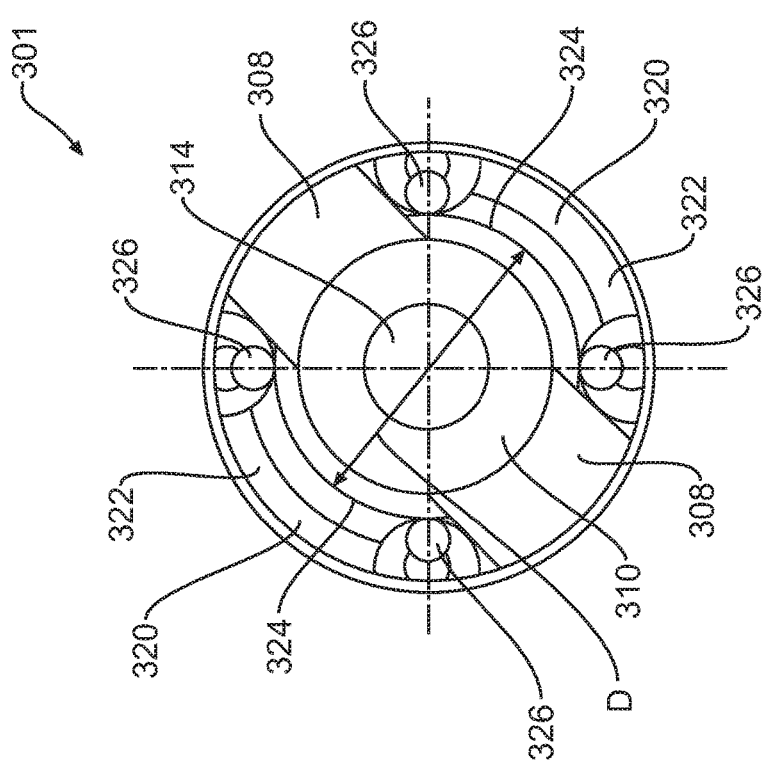
FIG. 6 is a front view of a body of a distal adapter, according to an exemplary embodiment.
Figure 7:
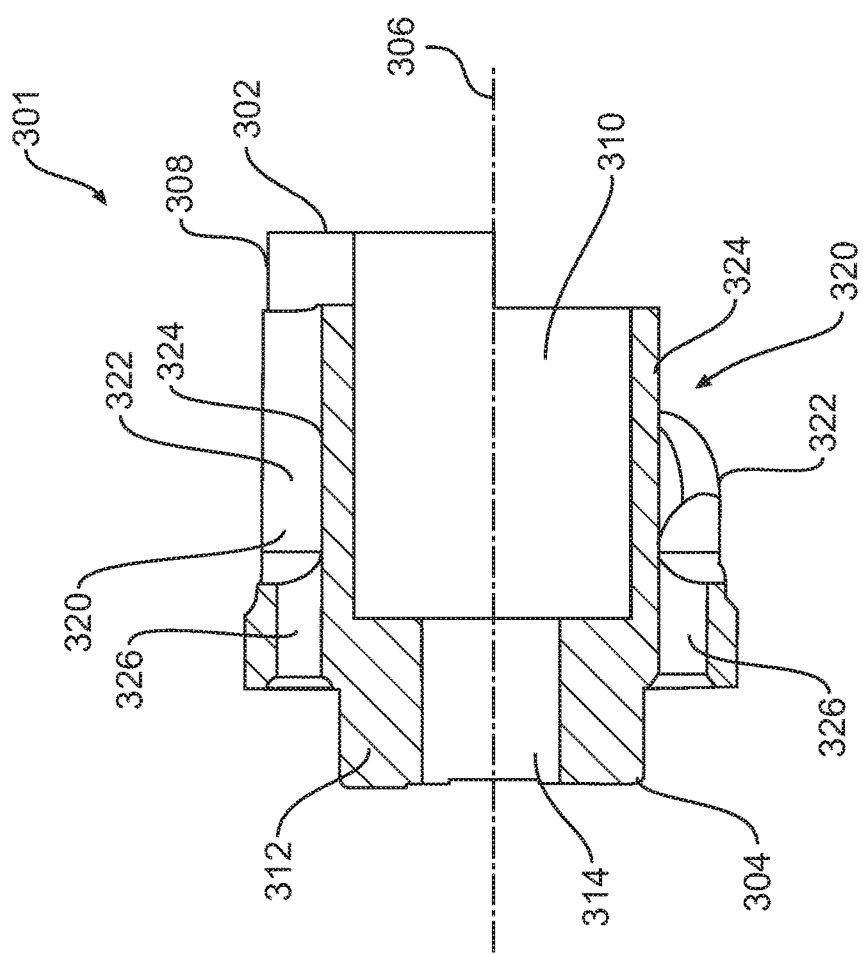
FIG. 7 is a cross-sectional side view of the body of the distal adapter of FIG. 6.
Figure 8:
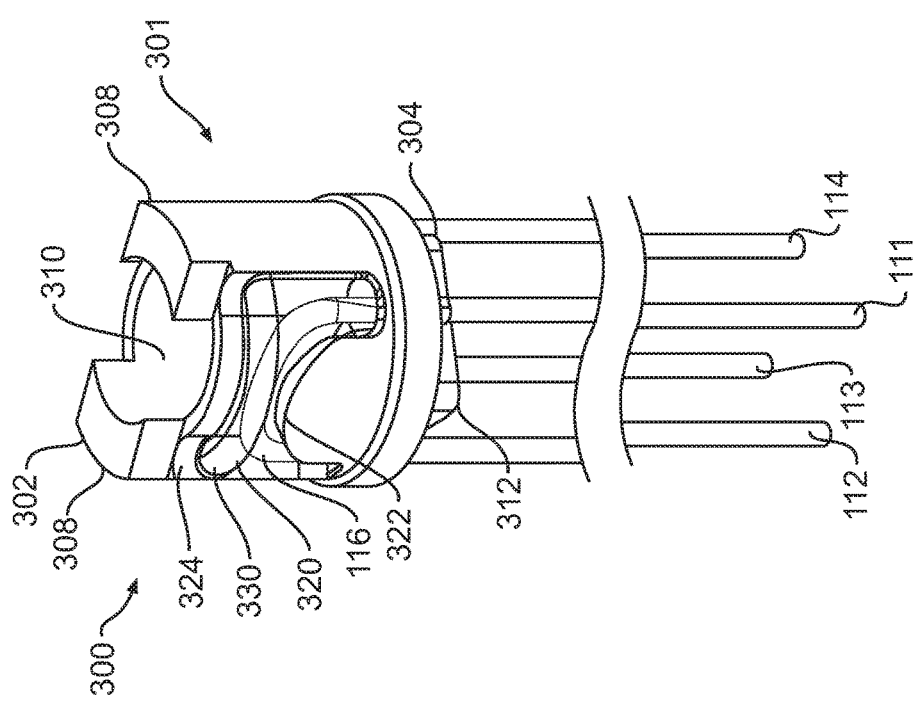
FIG. 8 is a perspective view of a distal adapter including the distal adapter body of FIG. 6.
Figure 9:
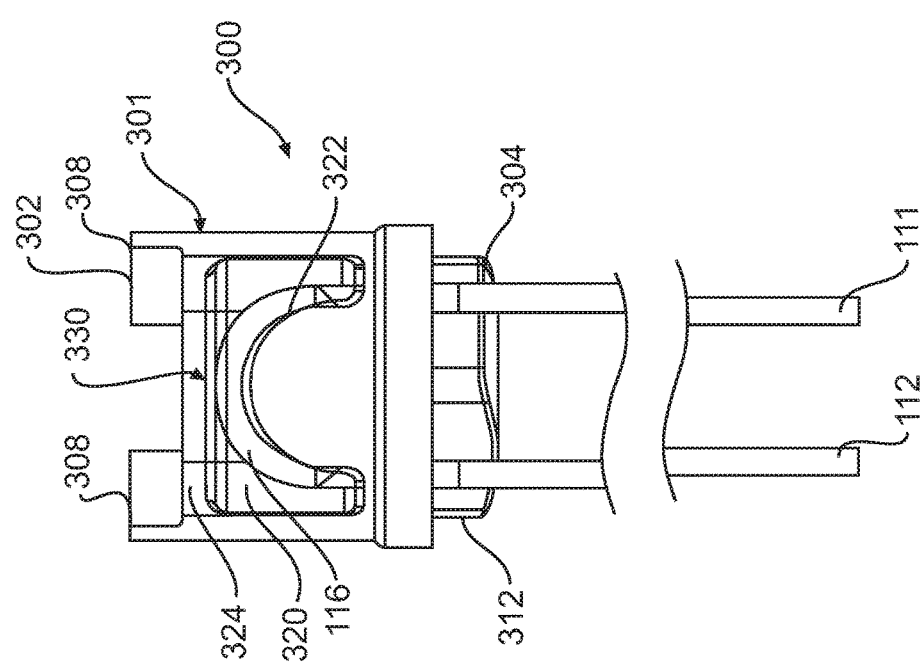
FIG. 9 is a side view of the distal adapter of FIG. 8.
Figure 10:
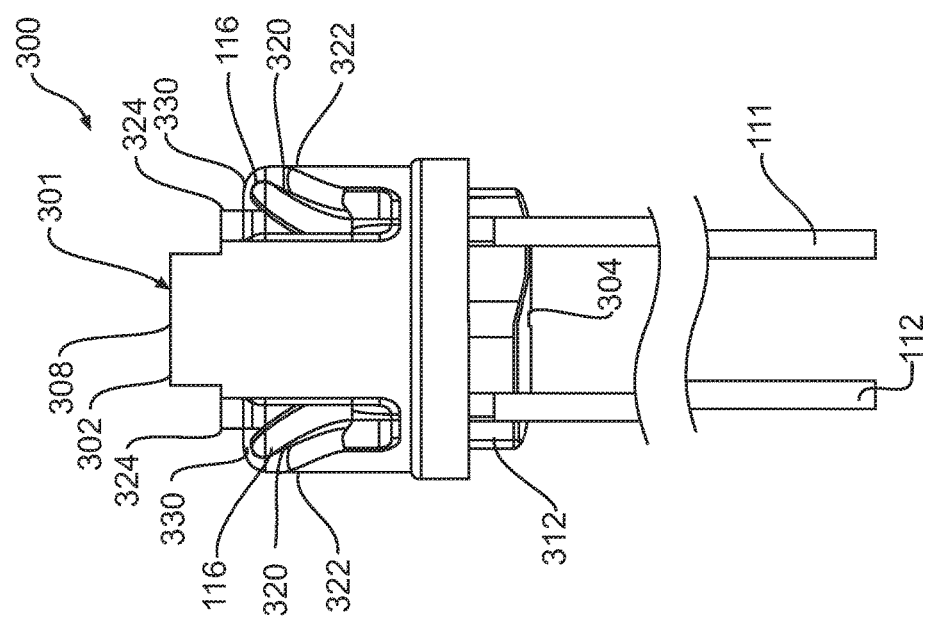
FIG. 10 is another side view of the distal adapter of FIG. 8.

FIGS. 6 and 7 show the body 301 of the distal adapter 300, according to another exemplary embodiment, and FIGS. 8-10 show the distal adapter 300 including the body 301 and two anchoring members 330, according to an exemplary embodiment. The body 301 includes a distal end 302, a proximal end 304, and a longitudinal axis 306 extending between the distal and proximal ends 302 and 304. In the exemplary embodiment, the body 301 may be formed of a rigid material, such as stainless steel or a polymer, such as a polyamid. Also, in an exemplary embodiment, the length or longitudinal dimension of the body 301 (e.g., the distance between the distal end 302 and the proximal end 304) may be less than or equal to approximately 0.16 inches.

The distal end 302 of the body 301 may include one or more distal protrusions 308 configured to engage and interlock with the proximal protrusions 208 (FIGS. 3 and 4) in the end effector 20. In the exemplary embodiment shown in FIGS. 5-10, the body 301 includes two distal protrusions 308. The two distal protrusions 308 may be disposed on opposite sides of the body 301 with respect to the longitudinal axis 306. The shape of the distal protrusions 308 may correspond to notches formed between the corresponding proximal protrusions 208 of the end effector 20. For example, each distal protrusion 308 may include one surface that may contact and be substantially flush against one proximal protrusion 208, and an opposite surface that may contact and be substantially flush against the other proximal protrusion 208. Engaging the proximal protrusions 208 with the distal protrusions 308 may permit torque transfer between the end effector 20 and the articulation section 30. The proximal protrusions 208 and the distal protrusions 308 may also be attached together (e.g., by welding or bonding) to attach the end effector 20 to the distal adapter 300.

The distal end 302 of the body 301 may also include a distal cavity 310. The distal cavity 310 may be configured to receive the proximal end of the actuator 206 of the end effector 20 when the actuator 206 is pulled in the proximal direction relative to the clevis 204 of the end effector 20, as described above.

The proximal end 304 of the body 301 may include a proximal protrusion 312 configured to be coupled or attached to the distalmost articulation link 400 of the series of articulation links 400. In the exemplary embodiment, the proximal protrusion 312 may be rectangular and may be received within a corresponding rectangular cavity in the distalmost articulation link 400. As shown in FIGS. 9 and 10, the proximal protrusion 312 may also include a curved proximal surface (e.g., concave or curved outward toward the proximal direction) to allow the distal adapter 300 to engage a corresponding curved surface (e.g., convex or curved inward) of the distalmost articulation link 400.

As shown in FIGS. 6 and 7, the body 301 of the distal adapter 300 may also include one or more actuator control member channels 314. In the exemplary embodiment, the body 301 includes one actuator control member channel 314 that has an axis that is substantially collinear with the longitudinal axis 306 of the body 301. The actuator control member channel 314 may connect to the distal cavity 310, which also has an axis that is collinear with the longitudinal axis 306 of the body 301 and may have a different width or lateral dimension (e.g., diameter) than the actuator control member channel 532. For example, as shown in FIGS. 6 and 7, the actuator control member channel 314 may have a smaller diameter than the distal cavity 310. The distal cavity 310 and the actuator control member channel 314 may slidably receive the actuator control member 102 (FIGS. 1, 3, and 4) to allow the actuator control member 102 to pass through the distal adapter 300.

The body 301 of the distal adapter 300 may also include one or more cavities 320 for supporting the one or more articulation control members received by the body 301. In the exemplary embodiment, the body 301 includes two side cavities 320 positioned at opposite sides of the body 301 relative to the longitudinal axis 306. Each side cavity 320 may be partially defined by a respective pedestal or ledge 322 and an inner surface 324. The inner surface 324 may extend generally along the direction of the longitudinal axis 306 and may have a diameter D (FIG. 6) measured along a plane perpendicular to the longitudinal axis 306. As shown in FIG. 6, the diameter D may be smaller than an outer diameter of the body 301. The ledges 322 may form a curved surface such that an outer surface of the curve faces the distal direction (e.g., concave or curved outward toward the distal direction).

In the exemplary embodiment shown in FIGS. 6-10, the ledges 322 and inner surfaces 324 may support the respective articulation control member (e.g., the bend portions 116) received in the body 301. Alternatively, in the exemplary embodiment shown in FIG. 5, the bend portions 116 may be supported by the inner surfaces 324 and may extend distal to the ledges 322. In both embodiments, the bend portions 116 may remain proximal to the distal end 302 of the body 301 without protruding from the distal end 302 of the body 301.

The distal adapter 300 may support the bend portions 116 of the articulation control members so that the articulation control members do not form a kink. In the exemplary embodiment shown in FIGS. 6-10, to reduce the likelihood of forming kinks, the ledges 322 may be formed as elliptical arcs (portions of ellipses), and the dimensions of the elliptical arcs may depend on a dimension of the distal adapter 300 (e.g., the diameter D (FIG. 6)) and/or a configuration of the articulation control member (e.g., the size of the braid). Alternatively, the ledges 322 may form another type of curved bend instead of an elliptical arc, such as a semicircular bend, the dimensions of which may also depend on a dimension of the distal adapter 300 and/or a configuration of the articulation control member.

Referring to FIGS. 6 and 7, each side cavity 320 may connect to one or more articulation control member channels 326. The articulation control member channels 326 may extend from the side cavities 320 to the outer surface of the body 301 from which the proximal protrusion 312 extends. In the exemplary embodiment shown in FIGS. 6-10, the body 301 includes four articulation control member channels 326 positioned at approximately 0, 90, 180, and 360 degrees, respectively, about the actuator control member channel 320 relative to the longitudinal axis 306. The articulation control member channels 326 may slidably receive the respective articulation control member portions 111, 112, 113, and 114 that are proximal to the bend portions 116 to allow the articulation control member portions 111, 112, 113, and 114 to extend in the proximal direction from the distal adapter 300.

FIGS. 8-10 show the anchoring members 330 disposed within the side cavities 320, respectively. The anchoring members 330 may be formed in the side cavities 320 after the articulation control members (e.g., the bend portions 116) are positioned on the respective ledges 322 and/or the inner surfaces 324. The anchoring members 330 may be attached to the body 301 by adhesion or cohesion, e.g., using an adhesive or a polymer. In an exemplary embodiment, the anchoring members 330 may be formed by epoxy (e.g., a one- or two-part epoxy) or other thermosetting polymer that may be inserted into and at least partially fill the side cavities 320 to fix the bend portions 116 to the ledges 322 and/or the inner surfaces 324. Alternatively, the anchoring members 330 may be formed by polyether ether ketone (PEEK), solder, or other material capable of melting at a temperature that is lower than the melting point of the material forming the body 301. In an exemplary embodiment, the anchoring members 330 may be formed so that an outer surface of the anchoring members 330 and an outer surface of the body 301 form a generally cylindrical outer surface, as shown in FIGS. 5 and 8-10. The anchoring members 330 may substantially cover the bend portions 116 and fix the bend portions 116 to the respective ledges 322 and/or inner surfaces 324. The anchoring members 330 may also be substantially entirely disposed between the distal or proximal ends 302 and 304.

In another exemplary embodiment, the proximal end of the clevis 204 may be received in and attached to, or uncoupled from, a distal end of the articulation section 30, in the manner shown in FIGS. 22-27B. For example, the proximal end of the clevis 204 may include a pair of arms and a shape and/or configuration similar to a proximal portion 740. The distal end of the distal adapter 300 may have shape and/or configuration similar to a distal portion 722. The proximal end of the clevis 204 and the distal end of the adapter 300 may have complementary shapes and/or configurations, similar to the proximal portion 740 and distal portion 722.

The actuator control member 102 may include a distal portion similar to a distal portion of an elongate member 726, and may also include a first fitting similar to a first fitting 730. The actuator 206 may include a proximal portion similar to a proximal portion of an actuator 738, and may also include a second fitting similar to the second fitting 732. The actuator 206 and the actuator control member 102 may couple and uncouple in the same way the elongate member 726 and the actuator 738 may couple The proximal end of the clevis 204 of the end effector 20 may be attached to the distal end of the distal adapter 300 by a securing member similar to a securing member 718. For example, a distal end of the securing member may include a retainer having a recess, similar to a distal end 758 of the securing member 718, a retainer 760, and a recess 761, respectively. The recess may be configured to receive a protrusion on a proximal portion of the clevis 204, similar to a protrusion 762 on a proximal portion 740 of a clevis 734. The securing member may move distally relative to the distal end of the distal adapter 300 when the proximal portion of the clevis 204 and the distal portion of the distal adapter 300 are aligned, to form a substantially cylindrical joint similar to a joint 763.

When the securing member is moved distally, the recess of the retainer may receive the protrusion on the proximal portion of the clevis 204, similar to the way the securing member 718 moves distally so the recess 761 of the retainer 760 may receive the protrusion 762 on the proximal portion 740 of the clevis 734. When the protrusion is received in the recess of the retainer, a radial force may be exerted on the first fitting and the second fitting to couple the first fitting and the second fitting, similar to coupling of the first fitting 730 and the second fitting 732. When the first and second fittings are coupled, the actuator 206 and the actuator control member 102 may be used to actuate the end effector 20. Further aspects that may be used in this embodiment, including connection features, and steps for coupling and uncoupling, are described below in sections referencing FIGS. 22-27B. It should be understood that any of the features in FIGS. 22-27B, either alone or in combination, may be used interchangeably with the features in FIGS. 1-21.

Figure 11:
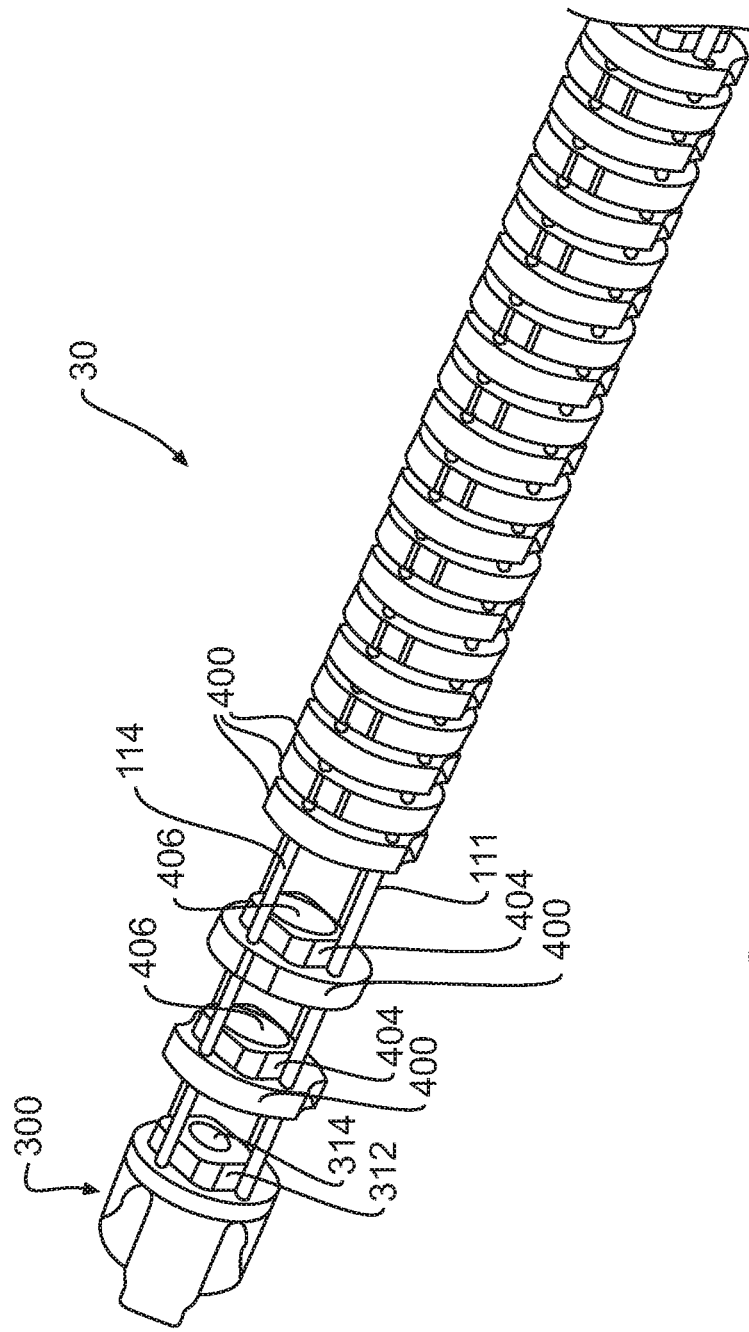
FIG. 11 is an exploded perspective view of an articulation section, according to an exemplary embodiment.

After fixing the articulation control members to the distal adapter 300, the articulation control member portions 111, 112, 113, and 114 may be inserted through corresponding channels in the plurality of articulation links 400 to allow the articulation control member portions 111, 112, 113, and 114 to pass through the articulation links 400. FIG. 11 shows the insertion of the articulation control member portions 111, 112, 113, and 114 through the plurality of articulation links 400 prior to positioning the articulation links 400 together as shown in FIG. 2. As shown in FIGS. 2 and 11, each articulation link 400 may include a substantially cylindrical outer surface, and may include a cavity 402 on its distal end and a protrusion 404 on its proximal end. Each articulation link 400 may also be coated with an insulative material. The protrusions 404 of each articulation link 400 may have a similar shape as the proximal protrusion 312 of the distal adapter 300. When the articulation control members connect the distal adapter 300 to the articulation links 400, the proximal protrusion 312 of the distal adapter 300 may be inserted into the cavity 402 in the distalmost (first) articulation link 400, the protrusion 404 on the first articulation link 400 may be inserted into the cavity 402 in the second articulation link 400, the protrusion 404 on the second articulation link 400 may be inserted into the cavity 402 in the third articulation link 400, etc. In an exemplary embodiment, the protrusions 404 of the articulation links 400 may be generally rectangular. The cavities 402 in the articulation links 400 may be defined by one or more inner surfaces, and may be generally rectangular in order to receive the corresponding protrusions 312, 404. Alternatively, the cavities 402 and protrusions 312, 404 may have another shape. The distal adapter 300, the articulation links 400, and the proximal adapter 500 allow the articulation section 30 to articulate as described above.

Each articulation link 400 may also include an inner surface defining one or more actuator control member channels 406. In the exemplary embodiment, each articulation link 400 includes one actuator control member channel 406 having an axis substantially collinear with a longitudinal axis of the articulation link 400 and extending through the articulation link 400. The actuator control member channel 406 may slidably receive the actuator control member 102 (FIGS. 1, 3, and 4) to allow the actuator control member 102 to extend between the end effector 20 and the proximal end 14 of the instrument assembly 10.

Figure 12:
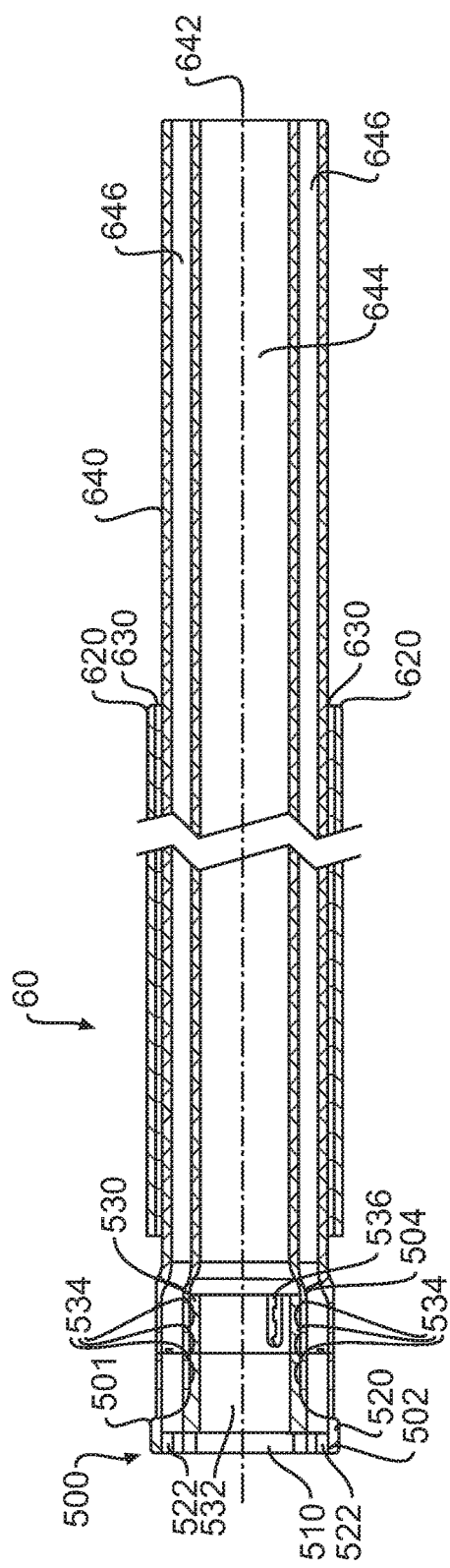
FIG. 12 is a cross-sectional side view of a proximal adapter of the articulation section attached to an instrument shaft section, according to an exemplary embodiment.
Figure 13:
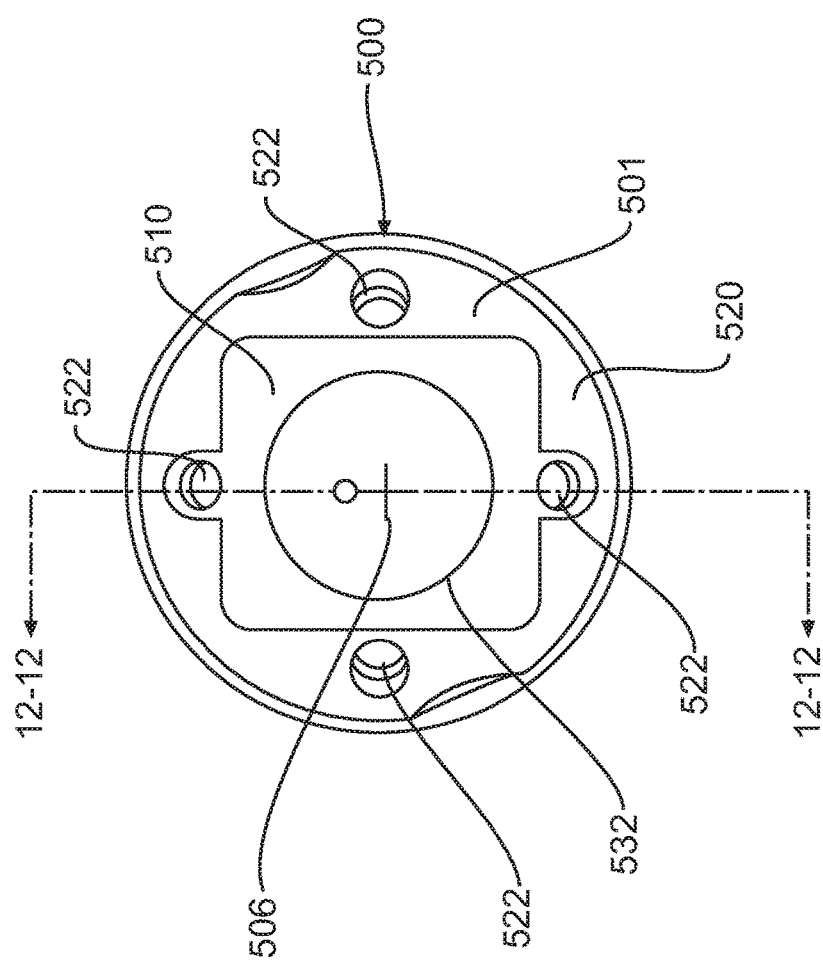
FIG. 13 is a front view of the proximal adapter and instrument shaft section of FIG. 12.

FIGS. 12 and 13 show the proximal adapter 500 of the articulation section 30. The proximal adapter 500 may connect to the distal end of the instrument shaft section 60. The proximal adapter 500 may include a body 501 including a distal end 502, a proximal end 504, and a longitudinal axis 506 extending between the distal and proximal ends 502 and 504. In the exemplary embodiment, the body 501 may be formed of a rigid material, such as stainless steel or a polymer, such as a polyamid. Also, in an exemplary embodiment, the length or longitudinal dimension of the body 501 may be less than or equal to approximately 0.12 inches.

The distal end 502 of the body 501 may include a distal cavity 510 sized to receive the protrusion 404 on the proximalmost articulation link 400. In the exemplary embodiment shown in FIGS. 12 and 13, the distal cavity 510 may be defined by one or more inner surfaces, and may have the same shape (e.g., rectangular) as the protrusion 404 on the proximalmost articulation link 400 in order to receive the protrusion 404.

The distal end 502 of the body 501 may also include a flange 520. The flange 520 may be generally cylindrical and may include a plurality of articulation control member channels 522 extending between the distal and proximal surfaces of the flange 520. In the exemplary embodiment, the flange 520 may include four articulation control member channels 522 that may be spaced from each other. For example, the four articulation control member channels 522 may be positioned at approximately 0, 90, 180, and 360 degrees, respectively, about the distal cavity 510 relative to the longitudinal axis 506, or at other angles. The articulation control member channels 522 may slidably receive the respective articulation control member portions 111, 112, 113, and 114 to allow the articulation control member portions 111, 112, 113, and 114 to pass through the proximal adapter 500.

The proximal end 504 of the body 501 may include a tubular portion 530 that extends from the flange 520 in the proximal direction. The tubular portion 530 may have a substantially cylindrical outer surface and may include an inner surface defining one or more actuator control member channels 532. In the exemplary embodiment shown in FIGS. 12 and 13, the body 301 may include one actuator control member channel 532 having an axis substantially collinear with the longitudinal axis 506 of the body 501. The actuator control member channel 532 may be substantially cylindrical and may connect to the distal cavity 510, which also has an axis that may be collinear with the longitudinal axis 506 of the body 501 and may have a different width or lateral dimension (e.g., diameter) than the actuator control member channel 532. For example, as shown in FIGS. 12 and 13, the actuator control member channel 532 may have a diameter that is smaller than the dimensions of the distal cavity 510. The distal cavity 510 and the actuator control member channel 532 may slidably receive the actuator control member 102 (FIGS. 1, 3, and 4) to allow the actuator control member 102 to extend between the end effector 20 and the proximal end 14 of the instrument assembly 10. In an exemplary embodiment, the length or longitudinal dimension of the tubular portion 530 (e.g., the distance between the proximal surface of the flange 520 to the proximal surface of the tubular portion 530) may be less than or equal to approximately 0.10 inches. As shown in FIG. 12, the tubular portion 530 of the proximal adapter 500 may be inserted into the instrument shaft section 60.

In an exemplary embodiment, the instrument shaft section 60 may include an outer first layer 610 (FIGS. 14-21), a second layer 620, a third layer 630, and a catheter or inner tubular portion 640 forming a fourth layer. The inner tubular portion 640 may be formed of a flexible material, such as a polymer, polyamide, etc. In an exemplary embodiment, the inner tubular portion 640 may be formed of nylon (e.g., nylon 12, RILSAN® AESNO) extruded to form the inner tubular portion 640.

As shown in FIG. 12, the inner tubular portion 640 may have a generally cylindrical outer surface and may have a longitudinal axis 642. The inner tubular portion 640 may also include a plurality of lumens or channels. For example, the inner tubular portion 640 may include one or more actuator control member channels 644, and one or more articulation control member channels 646. In the exemplary embodiment shown in FIG. 12, the inner tubular portion 640 includes one actuator control member channel 644 having an axis substantially collinear with the longitudinal axis 642. The actuator control member channel 644 may be generally cylindrical and may slidably receive the actuator control member 102 (FIGS. 1, 3, and 4). The tubular portion 530 of the proximal adapter 500 may be inserted into the actuator control member channel 644 of the inner tubular portion 640 so that the actuator control member channel 644 may align with the actuator control member channels 314, 406, and 532 in the distal adapter 300, the articulation links 400, and the proximal adapter 500. As a result, the actuator control member 102 may pass through the actuator control member channels 314, 406, 532, and 644 to extend between the end effector 20 and the proximal end 14 of the instrument assembly 10.

Also, the inner tubular portion 640 may include four articulation control member channels 646 that may be spaced from each other. For example, the four articulation control member channels 646 may be positioned at approximately 0, 90, 180, and 360 degrees, respectively, about the actuator control member channel 644 relative to the longitudinal axis 642, or at other angles. The articulation control member channels 646 may slidably receive the respective articulation control member portions 111, 112, 113, and 114. When the tubular portion 530 of the proximal adapter 500 is inserted into the inner tubular portion 640, the articulation control member channels 646 may align with the articulation control member channels 326 and 522 in the distal adapter 300, the articulation links 400, and the proximal adapter 500 to allow the articulation control member portions 111, 112, 113, and 114 to extend between the distal adapter 300 and the proximal end 14 of the instrument assembly 10.

The tubular portion 530 of the proximal adapter 500 may be inserted into the inner tubular portion 640 until a proximal surface of the flange 520 of the proximal adapter 500 abuts the distal end of the inner tubular portion 640.

The outer dimension (e.g., outer diameter) of the tubular portion 530 of the proximal adapter 500 may be larger than the dimension (e.g., diameter) of the actuator control member channel 644 of the inner tubular portion 640 before the tubular portion 530 is inserted into the inner tubular portion 640. Thus, although the inner tubular portion 640 may be formed with a substantially constant outer diameter and inner diameter, the insertion of the tubular portion 530 of the proximal adapter 500 may cause the inner tubular portion 640 to expand radially, as shown in FIG. 12. As a result, the inner tubular portion 640 may provide a radial pressure or force on the tubular portion 530 of the proximal adapter 500 such that the tubular portion 530 may be held in place in the inner tubular portion 640 (e.g., to assist in preventing the tubular portion 530 from inadvertently slipping out of the inner tubular portion 640).

The outer surface of the tubular portion 530 of the proximal adapter 500 may include one or more circumferential ribs 534. In the exemplary embodiment shown in FIG. 12, the tubular portion 530 includes three ribs 534, and the ribs 534 extend around substantially the entire circumference of the tubular portion 530. Alternatively, the ribs 534 may extend around a portion of the circumference. The ribs 534 may assist in maintaining the tubular portion 530 anchored in the inner tubular portion 640 of the instrument shaft section 60, e.g., by providing resistance to movement of the tubular portion 530 in the longitudinal direction.

The tubular portion 530 of the proximal adapter 500 may also include one or more notches 536. In the exemplary embodiment shown in FIG. 12, the tubular portion 530 includes one notch 536 extending generally parallel to the longitudinal axis 506 (FIG. 13). The notch 536 may extend along the radial direction through the tubular portion 530. The notch 536 may also extend along the longitudinal direction from the proximal end 504 of the body 501 past at least one of the ribs 534 (e.g., one, at least two, or all of the ribs 534). The notch 536 may assist in maintaining the tubular portion 530 anchored in the inner tubular portion 640 of the instrument shaft section 60, e.g., by providing resistance to torsional movement of the tubular portion 530.

The third layer 630 of the instrument shaft section 60 may be a reinforcement or stiffening layer that overlies the inner tubular portion 640. For example, the third layer 630 may include a braided configuration of tightly wound wires or polymeric elements, such as stainless steel braid. As shown in FIG. 12, the third layer 630 may cover a majority of the inner tubular portion 640 (e.g., an intermediate portion of the inner tubular portion 640), but may leave a portion of the inner tubular portion 640 uncovered (e.g., the distal end and/or the proximal end of the inner tubular portion 640). In an exemplary embodiment, the inner tubular portion 640 may be uncovered along a length of at least approximately 0.14 inches from the distal edge of the inner tubular portion 640. Alternatively, the length of the uncovered portion may depend on the length of the tubular portion 530 of the proximal adapter 500, e.g., so that the length of the uncovered portion is at least as long as the length of the tubular portion 530. As a result, the uncovered distal end of the inner tubular portion 640 may be free to expand, and may not be restricted by the third layer 630, the second layer 620, and/or any other additional layers, when the tubular portion 530 is inserted into the uncovered distal end of the inner tubular portion 640.

The second layer 620 of the instrument shaft section 60 may be formed of one or more polymers, such as a thermoplastic elastomer (e.g., PEBAX®). In an exemplary embodiment, the second layer 620 may be formed from PEBAX® 7233 or 6233. The second layer 620 may be formed by extrusion coating onto the third layer 630. As shown in FIG. 12, the second layer 620 may cover substantially the entire third layer 630.

As shown in FIGS. 14-21, the instrument shaft section 60 may also include the first layer 610. The first layer 610 may be formed of one or more fluoropolymers, such as fluorinated ethylene propylene (FEP), polytetrafluoroethylene (PTFE), perfluoroalkoxy (PFA), ethylene tetrafluoroethylene (ETFE), or other fluorinated material or fluoropolymer. Alternatively, or in addition, the first layer 610 may be formed of one or more other polymers, such as polyethylene, high-density polyethylene (HDPE), polyethylene terephthalate (PET), polyamide, etc. The first layer 610 may be formed by molding, heat shrinking, or extrusion onto the second layer 620. Alternatively, the first layer 610 may be formed by coating (e.g., dip coating) onto the second layer 620.

The first layer 610 may be formed of an insulative material, such as a material having a relatively high dielectric strength, a relatively low dielectric constant, and/or a relatively high melting temperature, such as FEP or other fluorinated material. Providing the first layer 610 over the third layer 630 (e.g., a stainless steel braided layer, according to an embodiment) may improve the insulation of the instrument assembly 10. For example, the first layer 610 may serve as a barrier that electrically insulates electrically conductive components in the instrument shaft section 60 (e.g., the third layer 630) from other components that may carry an electric current, such as a metal tip of an electrosurgical instrument used in conjunction with the instrument assembly 10. As a result, the first layer 610 may limit possible burning of the patient or damage to the instrument assembly 10 or the electrosurgical instrument due to the inadvertent conduction of electrical current.

Also, in an exemplary embodiment, the first layer 610 may have a higher dielectric strength, lower dielectric constant, and/or higher melting temperature than the second layer 620 (e.g., PEBAX®, according to an embodiment).

For example, the first layer 610 may be formed of FEP or other fluorinated material having a relatively low dielectric constant and a relatively high melting temperature (e.g., compared to PEBAX® or other material forming the second layer 620 or other portion of the instrument shaft section 60). The dielectric constant may correspond to the material's ability to polarize in an electric field. In a time-alternating electric field, molecules may heat up due to the reorientation of the molecules. A material with a relatively high dielectric constant and a relatively low melting temperature may heat up and exceed its melting temperature. Therefore, a material with a relatively low dielectric constant and a relatively high melting temperature may be desirable. For example, fluoropolymers having relatively low dielectric constants and relatively high melting temperatures include FEP (having a dielectric constant of approximately 2.1), PTFE (having a dielectric constant of approximately 2.1), PFA (having a dielectric constant of approximately 1.9 to approximately 2.1), and ETFE (having a dielectric constant of approximately 2.5 to approximately 2.6). Another polymer having a relatively low dielectric constant and relatively high melting temperature is polyethylene (having a dielectric constant of approximately 2.3). In comparison, PEBAX® has a dielectric constant of approximately 4.0. Accordingly, it may be desirable to form the first layer 610 of a material having a dielectric constant of less than approximately 3.0, or less than approximately 3.5. The dielectric constants identified above are provided for materials at a frequency of 1 MHz.

The first layer 610 may also provide a relatively high dielectric strength. For example, the first layer 610 may be formed of FEP or other fluorinated material having a relatively high dielectric strength (e.g., compared to PEBAX® or other material forming the second layer 620 or other portion of the instrument shaft section 60). The dielectric strength may correspond to the amount of voltage a material is able to withstand without breaking down. For example, the first layer 610 may be formed of FEP (having a dielectric strength that may be approximately 2000 V/inch in some applications), PFA (having a dielectric strength that may be approximately 2000 V/inch in some applications), or ETFE (having a dielectric strength that may be approximately 1800 V/inch in some applications). In comparison, PEBAX® may have a dielectric strength of approximately 1130 V/inch in some applications.

Optionally, additional layers may be provided between the first layer 610 and the inner tubular portion 640. For example, a layer or coating of PEBAX® 2533 or other thermoplastic elastomer, or other polymer may be provided between the third layer 630 and the inner tubular portion 640.

As shown in FIGS. 14-21, the articulation section 30 may also include a cover or sheath 410 that covers at least a portion of the articulation section 30 (e.g., the distal adapter 300, the articulation links 400, and/or the proximal adapter 500). The sheath 410 may be formed of one or more polymers, such as thermoplastic polyurethane (e.g., PELLETHANE®) or other polyurethane plastic or elastomer, or other thermoplastic elastomer, or other flexible polymer. The sheath 410 may be formed of a material, such as a layer of PELLETHANE®, that is relatively difficult to tear and is flexible.

The sheath 410 may act as a barrier between the patient and the components of the articulation section 30 (e.g., the distal adapter 300, the articulation links 400, and/or the proximal adapter 500). For example, the sheath 410 may limit occlusion formation in extracellular fluid (e.g., blood cell clumps) of the patient within the articulation section 30. Occlusions in the articulation section 30 may reduce the ability to articulate and/or actuate the instrument assembly 10.

The material used for forming the sheath 410 may be flexible. As the instrument assembly 10 articulates, the sheath 410 may be able to stretch and maintain a higher durometer (hardness) to prevent breakage of the sheath 410. As a result, the sheath 410 may be thinner, which may allow the operator to more easily insert the instrument assembly 10 in the patient.

Also, the sheath 410 may serve as a barrier that electrically insulates electrically conductive components in the articulation section 30 (e.g., the distal adapter 300, the articulation links 400, and/or the proximal adapter 500) from other components that may carry an electric current, such as a metal tip of an electrosurgical instrument used in conjunction with the instrument assembly 10. As a result, the sheath 410 may prevent possible burning of the patient or shocks to the surgeon due to the inadvertent conduction of electrical current through the instrument assembly 10.

As described below in connection with FIGS. 14-21, at least a portion of the sheath 410 may overlap and bond to at least a portion of the instrument shaft section 60, e.g., so that the sheath 410 and the first layer 610 of the instrument shaft section 60 can provide a continuous flexible and/or insulative barrier.

Depending on the materials used to form the sheath 410 and the first layer 610 of the instrument shaft section 60, it may be difficult to adhere the sheath 410 and the first layer 610 together. For example, inert or lubricious materials (e.g., materials having a low surface energy or coefficient of friction) may be difficult to adhere to other materials, and in an exemplary embodiment, the first layer 610 may be formed of a material, such as FEP or other fluorinated material, which is inert or lubricious. On the other hand, the instrument shaft section 60 may include other layers (e.g., the second layer 620, the inner tubular portion 640, etc.) formed of materials that may be less difficult to adhere to other materials. For example, the second layer 620 may be formed of PEBAX® and the inner tubular portion 640 may be formed of nylon.

FIGS. 14-21 show various exemplary embodiments in which the sheath 410 of the articulation section 30 may be attached to the instrument shaft section 60. The sheath 410 may include at least a portion 414, 416 (FIGS. 15, 17, 19, and 21) that overlaps and may be attached (e.g., using an adhesive) to a component of the instrument shaft section 60 that may be formed of a material that is not lubricious (e.g., a non-fluorinated material), as described below. As a result, the sheath 410 may be attached to the instrument shaft section 60 to form with the outer first layer 610 a continuous and flexible barrier to fluids and electrical current.

Figure 14:
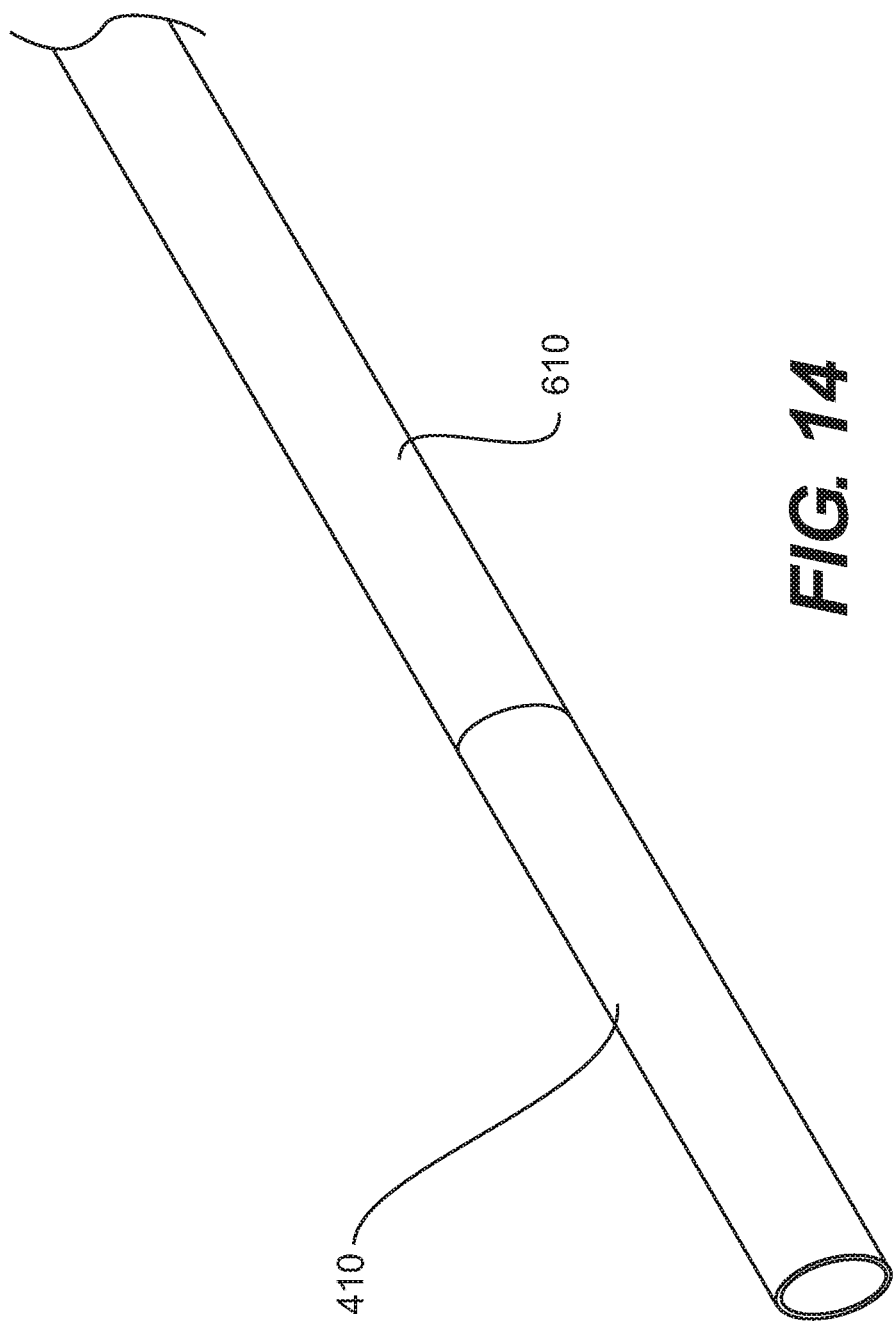
FIG. 14 is a perspective view of a sheath of an articulation section attached to an instrument shaft section, according to an exemplary embodiment.
Figure 15:
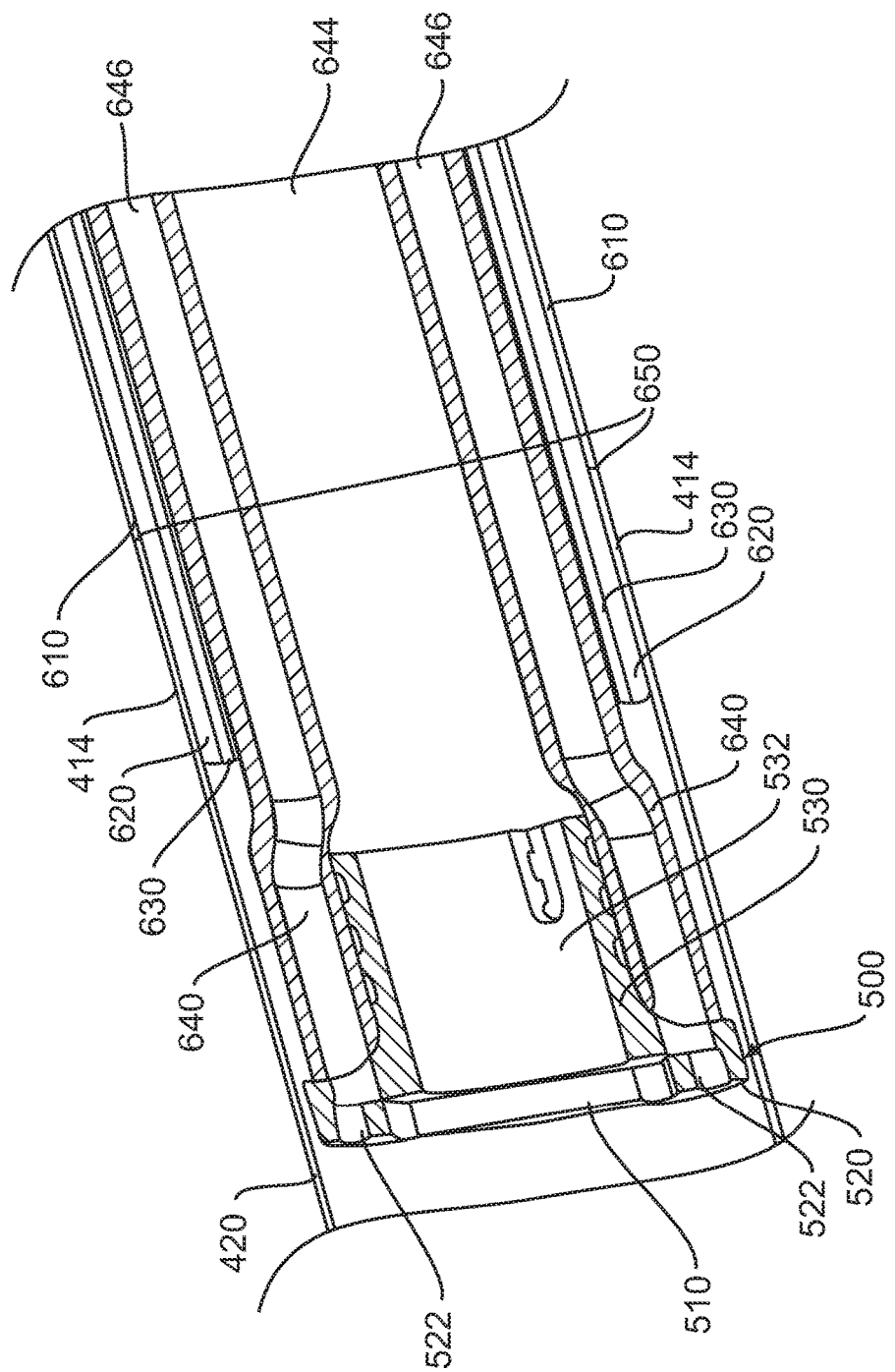
FIG. 15 is a cross-sectional perspective view of the sheath of the articulation section and the instrument shaft section of FIG. 14.

According to an embodiment, as shown in FIGS. 14 and 15, a proximal end portion 414 of the sheath 410 may be attached to the second layer 620 of the instrument shaft assembly 60.

The first layer 610 of the instrument shaft section 60 may be formed on the second layer 620 so that at least a portion of the second layer 620 (e.g., a distal end portion) is exposed. For example, the first layer 610 may be initially formed so that the entire second layer 620 is covered by the first layer 610. Then, the distal end portion of the first layer 610 may be removed (e.g., by centerless grinding or other removal method) to uncover the underlying portion of the second layer 620. Alternatively, the first layer 610 may be applied only on a proximal portion of the second layer 620.

Thus, prior to attaching the sheath 410 to the instrument shaft section 60, the distal end portion of the second layer 620 may be exposed. Then, the proximal end portion 414 of the sheath 410 may be placed over the exposed distal end portion of the second layer 620 so that the proximal edge of the sheath 410 may meet and abut a distal edge of the first layer 610 to form a meeting point or junction 650 between the sheath 410 and the first layer 610. The proximal end portion 414 of the sheath 410 may overlie the second layer 620 and may be bonded to the second layer 620, e.g. using an adhesive, such as a cyanoacrylate, an epoxy (e.g., a two-part epoxy), or an ultraviolet light curable adhesive. As a result, in the embodiment shown in FIGS. 14 and 15, the sheath 410, which may be formed of, e.g., PEL-LETHANE®, may be bonded to the second layer 620, which may be formed of a material that is not lubricious (e.g., PEBAX® or other non-fluorinated material).

In the embodiments shown in FIGS. 16-21 described below, the first layer 610 of the instrument shaft section 60 may cover substantially the entire second layer 620. The portion 414 or 416 of the sheath 410, which may be formed of, e.g., PELLETHANE®, may be bonded to the inner tubular portion 640 of the instrument shaft assembly 60, which may be formed of a material that is not lubricious (e.g., nylon or other non-fluorinated material).

Figure 16:
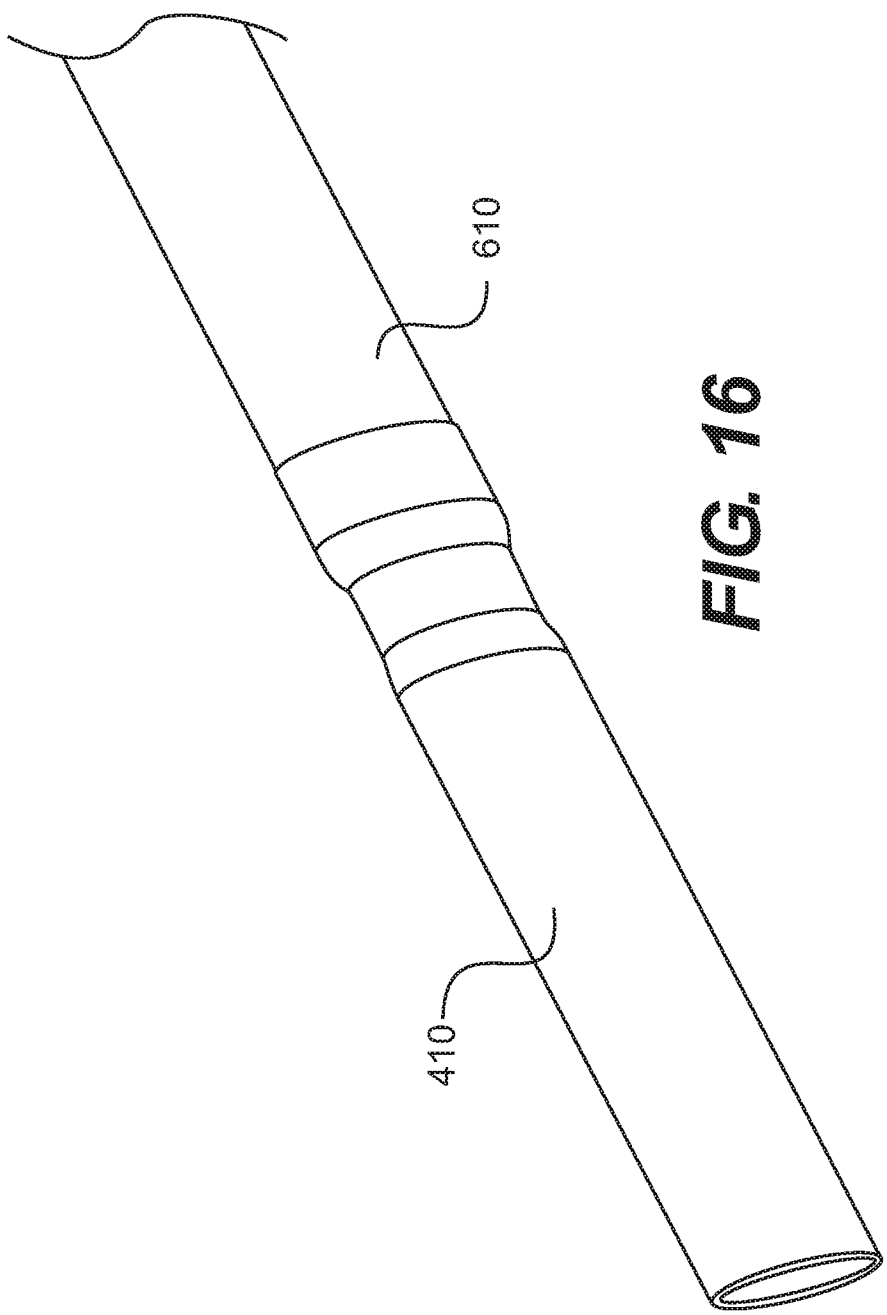
FIG. 16 is a perspective view of a sheath of an articulation section attached to an instrument shaft section, according to another exemplary embodiment.
Figure 17:
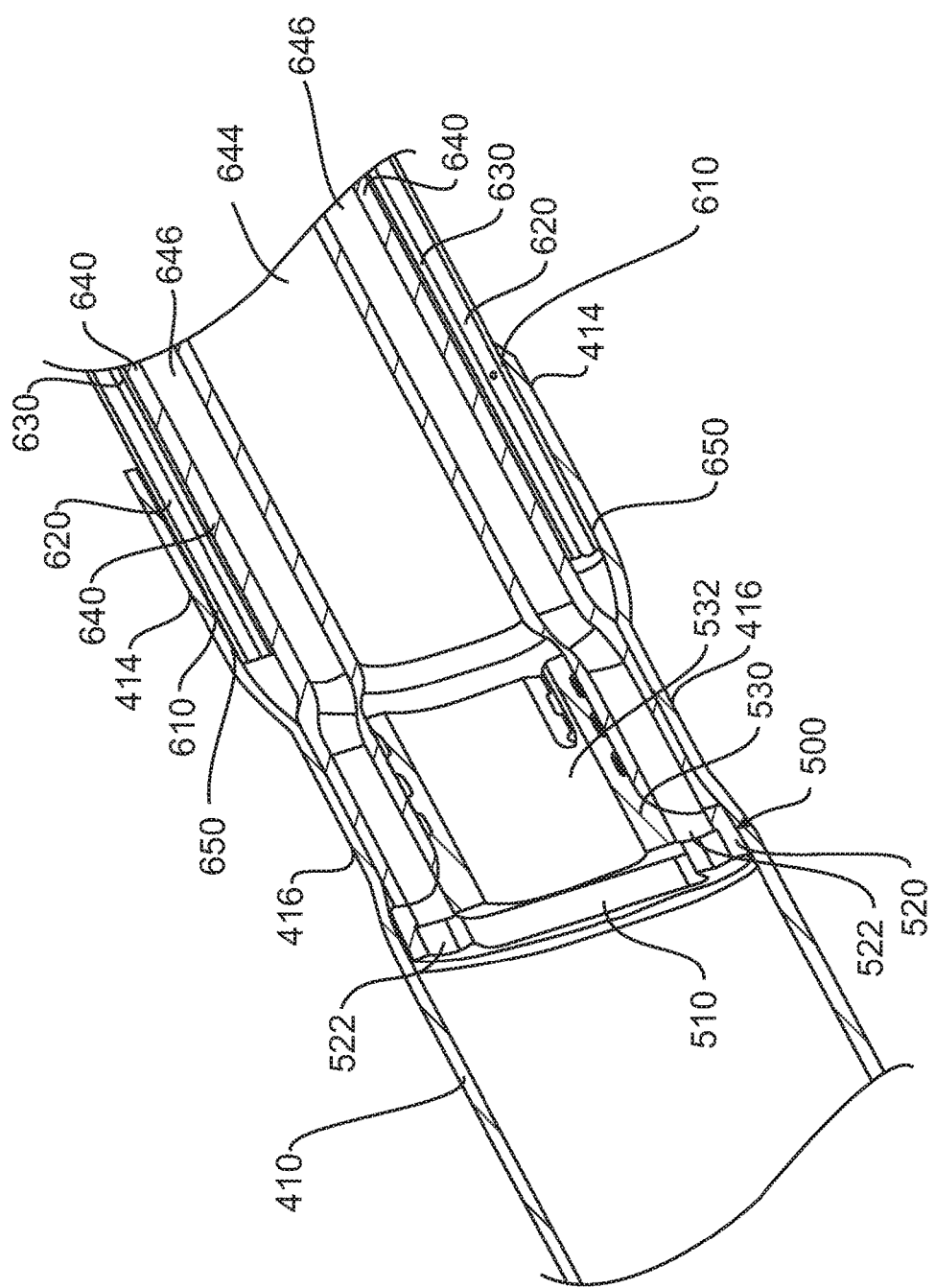
FIG. 17 is a cross-sectional perspective view of the sheath of the articulation section and the instrument shaft section of FIG. 16.

In the embodiment shown in FIGS. 16 and 17, the proximal end portion of the sheath 410 may extend over the distal end portion of the first layer 610 of the instrument shaft section 60 to form the junction 650 between the sheath 410 and the first layer 610. An intermediate portion 416 of the sheath 410 may overlie and be bonded to the exposed portion of the inner tubular portion 640 of the instrument shaft assembly 60 (e.g., the portion of the inner tubular portion 640 that is radially expanded due to the insertion of the tubular portion 530 of the proximal adapter 500). The intermediate portion 416 may be bonded using an adhesive, such as a cyanoacrylate, a two-part epoxy, or an ultraviolet light curable adhesive.

Also, at the junction 650 formed by the meeting of the proximal end portion of the sheath 410 with the distal end portion of the first layer 610, the proximal end portion of the sheath 410 may form a seal with the first layer 610. For example, the sheath 410 may be formed of a stretchable or elastic material (e.g., PELLETHANE®) that provides a compressive radial pressure on the overlapped portion of the first layer 610. Alternatively, or in addition, the distal end portion of the first layer 610 may be treated (e.g., plasma treated, chemically etched, etc.) and bonded to the proximal end portion of the sheath 410 (e.g., using an adhesive). As another alternative, the distal end portion of the first layer 610 and/or the proximal end portion of the sheath 410 may be roughened to increase the surface areas of the respective portions, and the roughened portions may be bonded together (e.g., using an adhesive). Roughening the respective portions may provide increased surface area (e.g., valleys) for the adhesive to contact.

Figure 18:
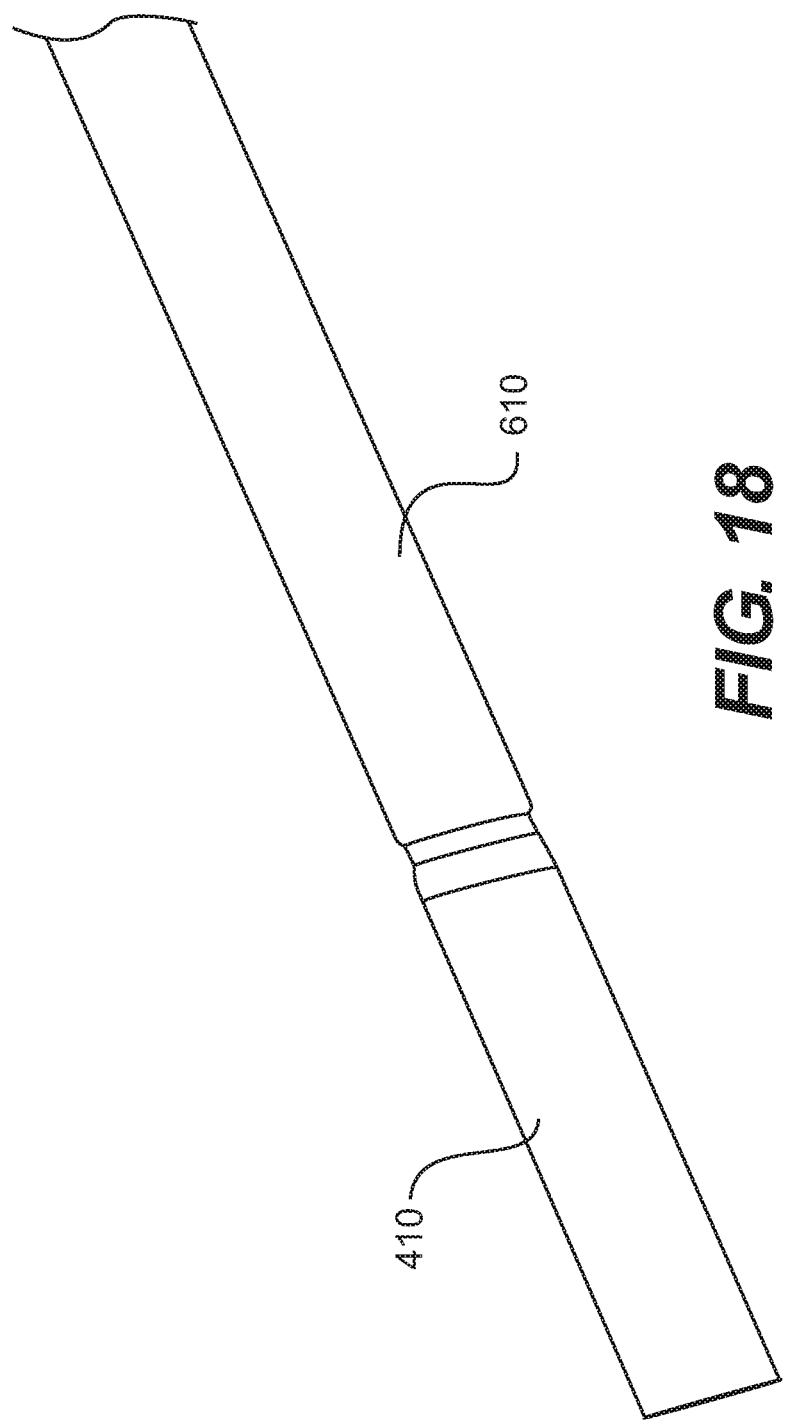
FIG. 18 is a perspective view of a sheath of an articulation section attached to an instrument shaft section, according to a further exemplary embodiment.
Figure 19:
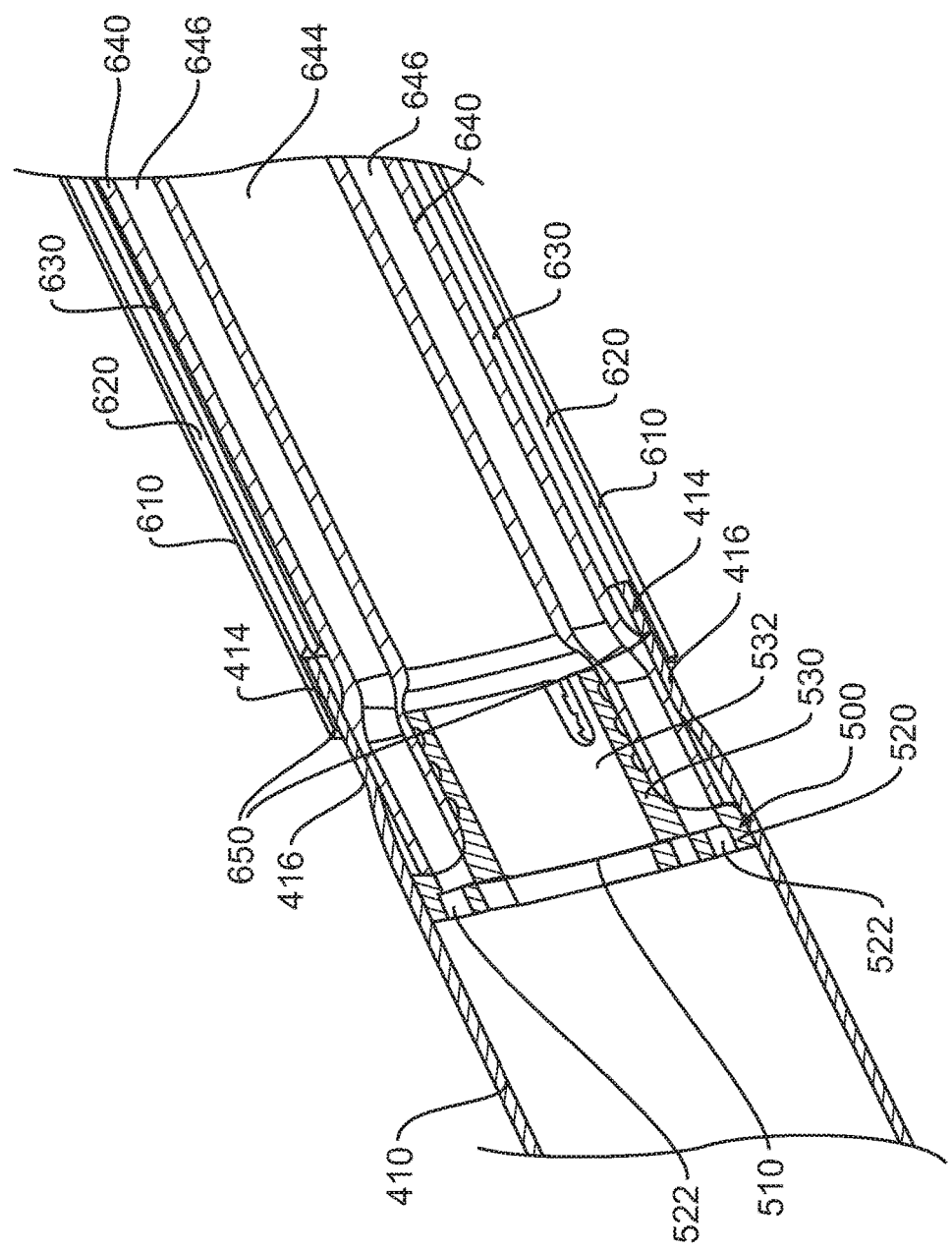
FIG. 19 is a cross-sectional perspective view of the sheath of the articulation section and the instrument shaft section of FIG. 18.

According to another embodiment, as shown in FIGS. 18 and 19, the first layer 610 of the instrument shaft section 60 may include a distal end portion that extends past the second and third layers 620 and 630 in the distal direction, without covering a distal end portion of the inner tubular portion 640. The distal end portion of the first layer 610 that extends past the second and third layers 620 and 630 may form the junction 650 between the sheath 410 and the first layer 610 of the instrument shaft section 60.

The proximal end portion 414 of the sheath 410 may extend over the distal end portion of the inner tubular portion 640. The proximal end portion 414 of the sheath 410 may meet and abut the distal edge of the second layer 620 and/or a distal edge of the third layer 630. The intermediate portion 416 of the sheath 410 may overlie and be bonded to the exposed portion of the inner tubular portion 640 of the instrument shaft assembly 60 (e.g., the portion of the inner tubular portion 640 that is radially expanded due to the insertion of the tubular portion 530 of the proximal adapter 500). The intermediate portion 416 of the sheath 410 may be bonded to the inner tubular portion 640, e.g. using an adhesive, such as a cyanoacrylate, a two-part epoxy, or an ultraviolet light curable adhesive.

Also, at the junction 650 formed by the meeting of the proximal end portion of the sheath 410 with the distal end portion of the first layer 610, the proximal end portion of the sheath 410 may form a seal with the first layer 610. For example, the first layer 610 may be formed of a stretchable or elastic material (e.g., FEP) that provides a compressive radial pressure on the overlapped portion of the sheath 410. Alternatively, other methods as described above, e.g., plasma treatment, chemical etching, surface roughening and bonding, etc., may be used to form the seal.

Figure 20:
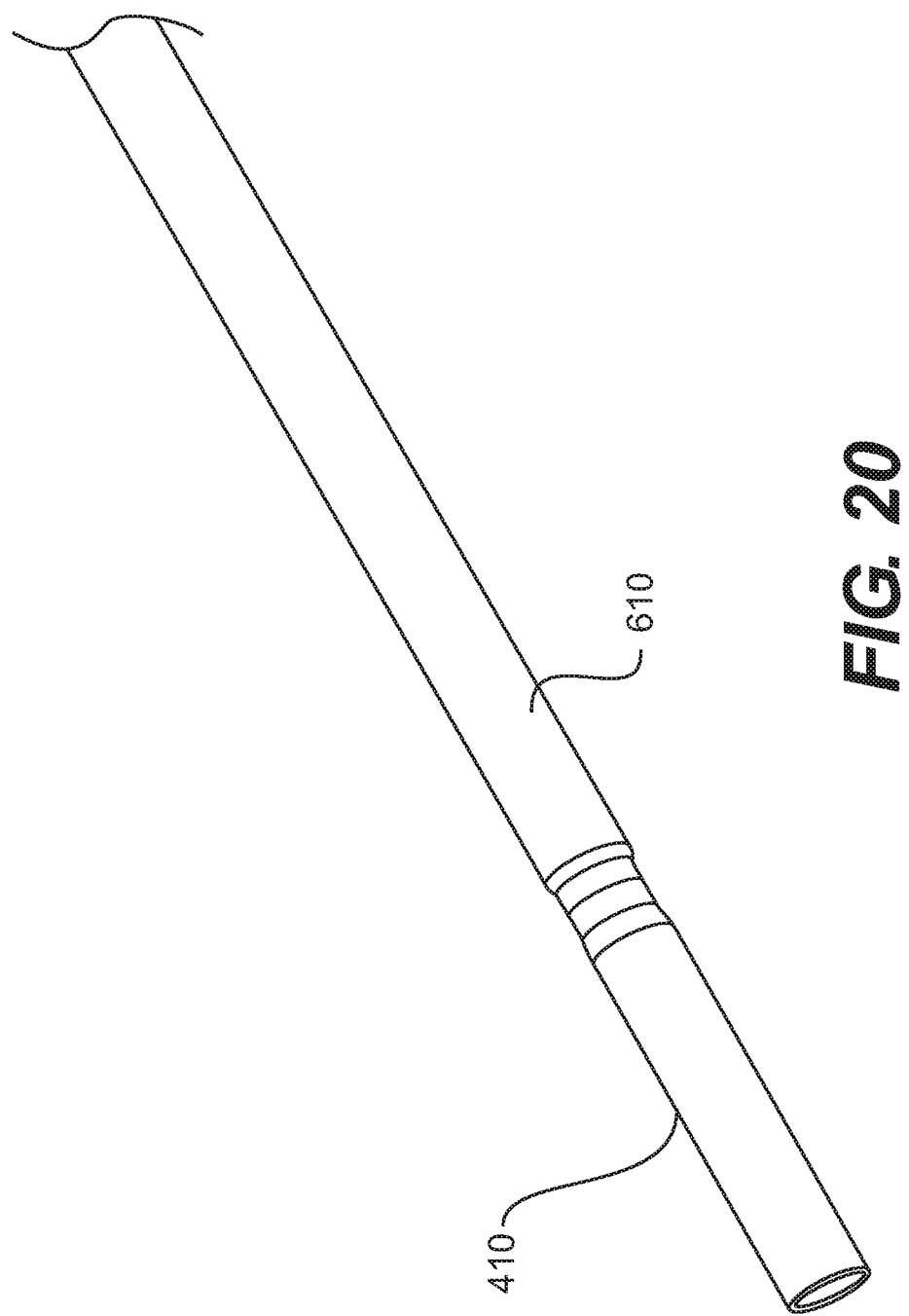
FIG. 20 is a perspective view of a sheath of an articulation section attached to an instrument shaft section, according to yet another exemplary embodiment.
Figure 21:
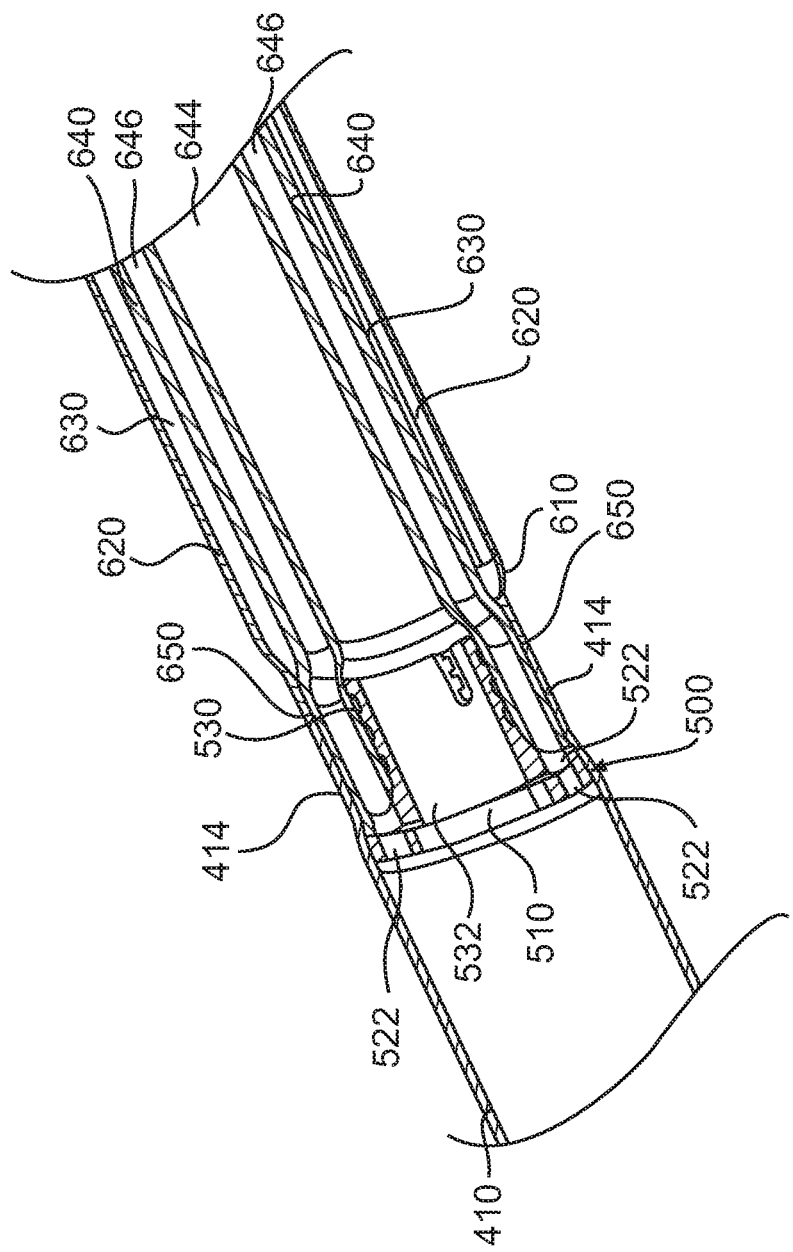
FIG. 21 is a cross-sectional perspective view of the sheath of the articulation section and the instrument shaft section of FIG. 20.

According to another embodiment, as shown in FIGS. 20 and 21, the first layer 610 of the instrument shaft section 60 may include a distal end portion that extends past the second and third layers 620 and 630 in the distal direction, without covering a distal end portion of the inner tubular portion 640, similar to the embodiment shown in FIGS. 18 and 19. For example, to form the first layer 610 so that the distal end portion extends past the second and third layers 620 and 630 in the distal direction, distal end portions of the second and third layers 620 and 630 may be removed prior to forming the first layer 610 on the second layer 620 (e.g., by centerless grinding or other removal method). Alternatively, other methods may be used to provide the first layer 610 that extends past the second and third layers 620 and 630 in the distal direction.

The distal end portion of the first layer 610 that extends past the second and third layers 620 and 630 may form the junction 650 between the sheath 410 and the first layer 610 of the instrument shaft section 60. However, instead of overlapping the sheath 410 as shown in the embodiment shown in FIGS. 18 and 19, the first layer 610 may meet and abut a proximal edge of the sheath 410 to form the junction 650 between the sheath 410 and the first layer 610 of the instrument shaft section 60. The proximal end portion 414 of the sheath 410 may overlies the exposed portion of the inner tubular portion 640 and may be bonded to the inner tubular portion 640, e.g. using an adhesive, such as a cyanoacrylate, a two-part epoxy, or an ultraviolet light curable adhesive.

The distal end portion of the first layer 610 that extends past the second and third layers 620 and 630 may also overlie the exposed portion of the inner tubular portion 640.

The distal end portion of the first layer 610 may form a seal with the inner tubular portion 640. For example, the distal end portion of the first layer 610 may be bonded to the inner tubular portion 640, e.g. using an adhesive, such as a cyanoacrylate, a two-part epoxy, or an ultraviolet light curable adhesive. Alternatively, the first layer 610 may be formed of a stretchable or elastic material (e.g., FEP) that provides a compressive radial pressure on the overlapped portion of the inner tubular portion 640. Alternatively, other methods as described above, e.g., plasma treatment, chemical etching, surface roughening and bonding, etc., may be used to form the seal.

As a result, in an embodiment in which the third layer 630 is formed of stainless steel braid or other braided configuration of electrically conductive material, the third layer 630 may be provided at a distance from the junction 650 between the sheath 410 and the first layer 610 of the instrument shaft section 60, thereby assisting in preventing electrons from arcing through the junction 650 and being transmitted through the third layer 630. Providing the third layer 630 at a distance from the junction 650 may also assist in securing any wires in the third layer 630 (which may also be ground down) under the first layer 610, e.g., so that the wires do not extend through the junction 650 and scratch the patient, guide tube, or other structure for receiving the instrument assembly 10.

Figure 22:
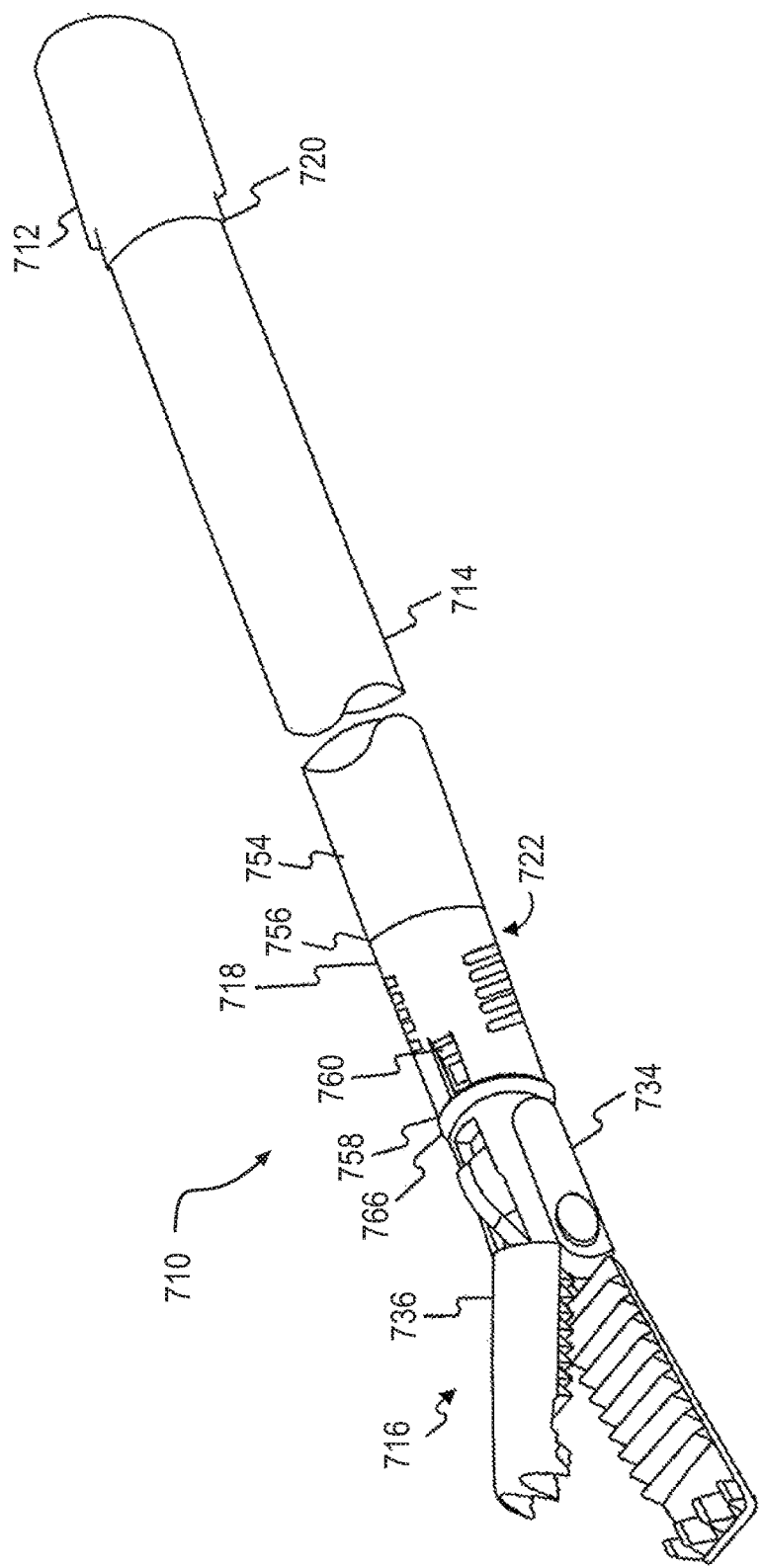
FIG. 22 is a perspective view of a medical device in an attached configuration, according to an exemplary embodiment of the disclosure.

FIG. 22 illustrates a medical device 710, according to an exemplary embodiment. Medical device 710 may be configured for use with a surgical method, including a therapeutic or diagnostic procedure. For example, medical device 710 may be configured for use with an endoscope, a laparoscope, a utereroscope, a guide tube, an access catheter, or any other type of device configured to access a patient's body. Medical device 710 may be used for procedures within or adjacent to various body organs, such as, an esophagus, a heart, a stomach, a pelvic area, a bladder, an intestine, or any other portion of a gastrointestinal, urinary, pulmonary tract, or body.

Medical device 710 may be configured for insertion into a patient's body through an anatomical opening. In some embodiments, medical device 710 may be used in natural orifice transluminal endoscopic surgery (NOTES) procedures or percutaneous procedures such as single incision laparoscopic surgical (SILS) procedures. Accordingly, medical device 710 may be shaped and sized for placement into a patient via a body cavity or an incision.

Medical device 710 may include a handle portion 712, a shaft 714, an end-effector assembly 716, and a securing member 718. Shaft 714 may have a proximal end 720 and a distal portion 722. For purposes of this disclosure, "proximal" refers to the end closer to the device operator during use, and "distal" refers to the end further from the device operator during use. Handle portion 712 may be disposed at proximal end 720 of shaft 714. Handle portion 712 may be any suitable, known handle including spool-type handles or scissor-type handles. As shown in FIG. 22, end-effector assembly 716 may be aligned with and connected to distal portion 722 of shaft 714.

Figure 23:
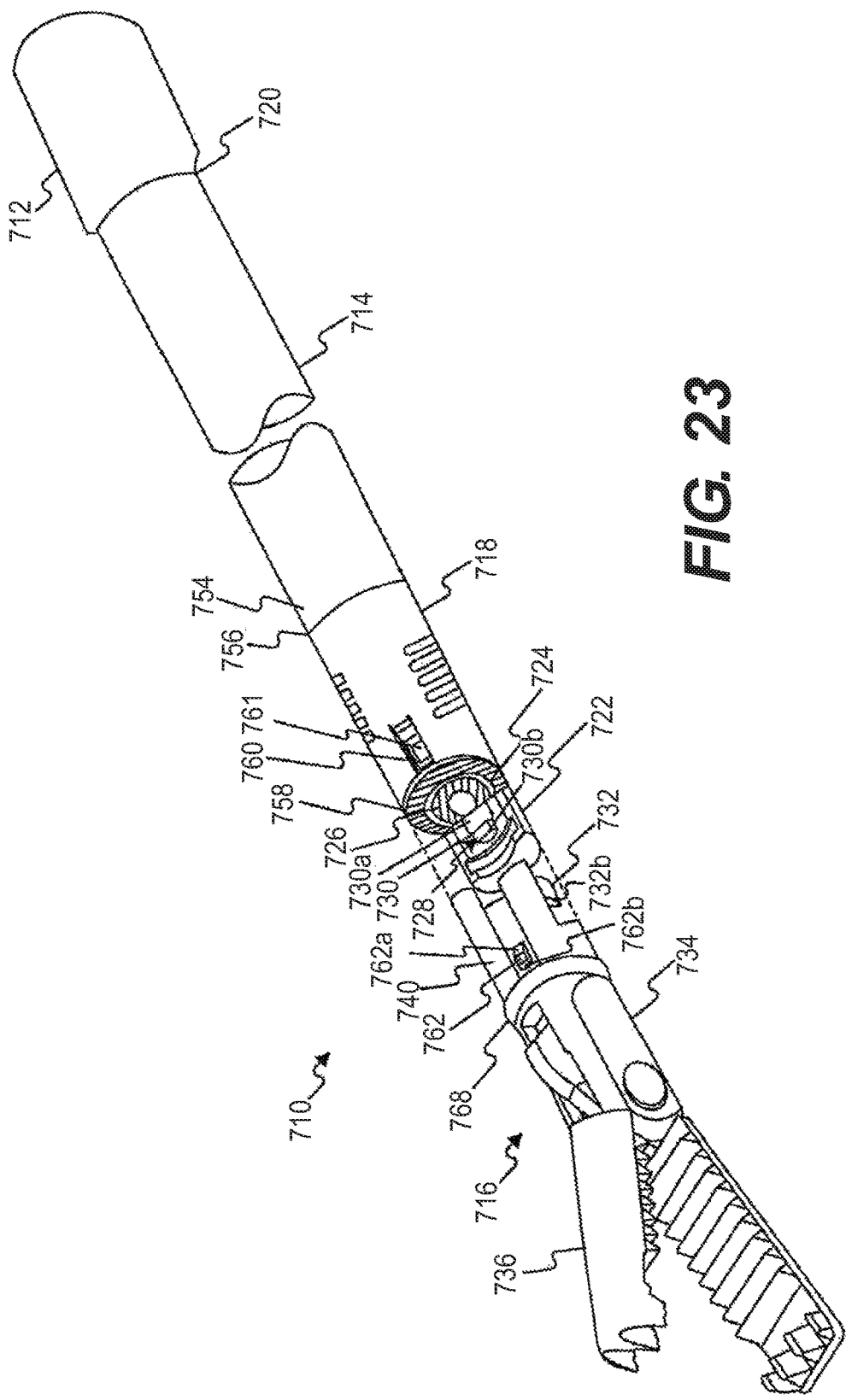
FIG. 23 is a perspective view of the medical device of FIG. 22 in a detached configuration, according to an exemplary embodiment of the disclosure.

Medical device 710 is shown in FIG. 23 in a detached configuration, whereby end-effector assembly 716 is shown separated from distal portion 722 of shaft 714. As described herein, end-effector assembly 716 and distal portion 722 of shaft 714 are configured for releasable engagement. Specifically, end-effector assembly 716 may be connected to distal portion 722 of shaft 714 by securing member 718 to allow a user to control movement, actuation, and/or operation of end-effector assembly 716 via handle portion 712. End-effector assembly 716 may also be disconnected from distal portion 722 of shaft 714 so that other end-effector assemblies (either the same or different types) may be connected to distal portion 722 of shaft 714.

In some embodiments, handle portion 712 and shaft 714 may be reusable and end-effector assembly 716 may be disposable. Multiple end-effector assemblies, having different end-effectors, may be used interchangeably with a single shaft 714 and handle portion 712. It is contemplated that the various end-effector assemblies could be provided together in kit form.

Shaft 714 may be a flexible or rigid tube, made from any suitable biocompatible material known to one of ordinary skill in the art. Such materials may include, but are not limited to, rubber, silicon, plastics, stainless steel, metal-polymer composites, and metal alloys of nickel, titanium, copper cobalt, vanadium, chromium, and iron. In one embodiment, the material forming shaft 714 may be a superelastic material such as nitinol, which is a nickel-titanium alloy. In some embodiments, shaft 714 may include layers of different materials and reinforcements such as braiding or coiling within the wall of shaft 714. Shaft 714 may have any cross-sectional shape and/or configuration and may be any desired dimension that can be received in a body cavity. In some embodiments, shaft 714 may be made of, or coated with, a polymeric or lubricious material to enable medical device 710 to pass through a body cavity with ease. Additionally, shaft 714 may be steerable and may have areas of different flexibility or stiffness to promote steerability with the body cavity. Steerability may, for example, be controlled by wires.

Shaft 714 may include a lumen 724 extending distally from proximal end 720 of shaft 714 to distal portion 722 of shaft 714. It is to be understood that lumen 724 may have any size, cross-sectional area, shape, and/or configuration. An elongate member 726 may be disposed in lumen 724, and may be configured to move relative to shaft 714. Elongate member 726 may include a proximal end (not shown) and a distal end 728, and may comprise malleable, flexible, and/or rigid portions. In some embodiments, elongate member 726 may be a cable, wire, or similarly flexible material extending distally from handle portion 712 to distal portion 722. Elongate member 726 may have any desired cross-sectional shape and/or configuration that can be received within lumen 724 of shaft 714.

As shown in FIGS. 2 and 5C, distal end 728 of elongate member 726 may extend into distal portion 722 of shaft 714 and may define a first fitting 730. In some embodiments, first fitting 730 may have an L-shaped cross-sectional configuration with a first groove 730a and a first enlargement 730b.

As shown in FIG. 24A, end-effector assembly 716 may be provided separately from shaft 714 and handle portion 712, and may include an assembly of multiple components including a clevis 734, a pair of end-effectors 736, and an actuator 738.

Clevis 734 may be, for example, machined or formed as a unitary mold or cast member, or may be stamped from a steel sheet and formed (by e.g., rolling) into an appropriate configuration. Clevis 734 may include a proximal portion 740 and a pair of arms 742 extending from proximal portion 740. Proximal portion 740 of clevis 734 and distal portion 722 of shaft 714 may have complementary shapes and/or configurations. In an exemplary embodiment, proximal portion 740 of clevis and distal portion 722 of shaft 714 may each form half-cylindrical portions. It is contemplated that proximal portion 740 of clevis 734 and distal portion 722 of shaft 714 may form any other set of complementary shapes and/or configurations, including lock and key configurations.

Arms 742 of clevis 734 may extend distally from proximal portion 740. Arms 742 may be substantially similar in shape, however, they may also have different shapes or configurations. Each arm 742 may have an axle hole 744 for receiving an axle pin 743. The pair of end-effectors 736 may be inserted in a slot between arms 742 and mounted to clevis 734 by axle pin 743. In the illustrated embodiment, the pair of end-effectors 736 may be graspers. It is contemplated, however, that the pair of end-effectors 736 may be cutting blades, forceps, graspers, dissectors, scissors, biopsy forceps, or other types of tools.

As illustrated in FIG. 24B, proximal portion 740 of clevis 734 may include a throughhole 749 which receives actuator 738. Actuator 738 may have a proximal end 752 and a pair of arms 750 extending distally from proximal end 752 of actuator 738. Proximal end 752 of actuator 738 may extend into proximal portion 740 of clevis 734, and may include a second fitting 732 configured to be aligned with and coupled to first fitting 730. In some embodiments, second fitting 732 may have an L-shaped cross-sectional configuration with a second groove 732a and a second enlargement 732b, with similar sizes, shapes, and/or configurations as first groove 730a and first enlargement 730b of first fitting 730. Second enlargement 732b may be received in first groove 730a and first enlargement 730b may be received in second groove 732a, so as to couple first fitting 730 and second fitting 732. It will be appreciated that any number of tabs and/or protrusions may be disposed on first fitting 730 and second fitting 732 to fit, snap, or connect into a complementary recess or hole in second fitting 732 and first fitting 730.

In some embodiments, first fitting 730 and second fitting 732 may form a ball and socket coupling configuration. In particular, first fitting 730 or second fitting 732 may form a ball and the other of first fitting 730 and second fitting 732 may form a socket. In other embodiments, first fitting 730 and second fitting 732 may have a dove-tail, detent pin, or snap ring designs. It is contemplated that first fitting 730 and second fitting 732 may have any other set of complementary shapes, configurations, and/or designs to facilitate coupling of first fitting 730 and second fitting 732.

In one embodiment, arms 750 of actuator 738 may extend into a slot formed between arms 742 of clevis 734. Arms 750 may be substantially similar in shape, however, they may have different shapes or configurations. A tang 746 of each end-effector 736 may be disposed between arms 750 of actuator 738. As shown in FIG. 24C, each end effector 736 may include a slot 747 formed in tang 746. A pin 751 may extend through slot 747 to mount end effectors 736 to arms 750 of actuator 738. When pin 751 is in a proximalmost position in slot 747 of each end effector 736, the pair of end-effectors 736 may be in a closed configuration. Distal movement of actuator 738 may cause pin 751 to ride distally in slot 747. In doing so, the pair of end-effectors 736 may pivot about pin 743 to translate the pair of end-effectors 736 to an open configuration.

Referring to FIG. 25, securing member 718 may comprise a tube formed of any rigid, malleable, or flexible material. In one embodiment, the material forming securing member 718 may be a stainless steel sleeve or a superelastic material such as nitinol, which is a nickel-titanium alloy. Securing member 718 may have a shape such as a cylindrical shape, and may be sized to conform to an exterior 754 of device 710. In some embodiments, securing member 718 may fit around a portion of the perimeter of device 710 without completely extending around the entire circumference of device 710. It is contemplated, that securing member 718 may have any other shape, size, cross-sectional area, and/or configuration. In the exemplary embodiment illustrated in FIG. 25, securing member 718 is disposed on an exterior of shaft 714, however, securing member 718 may be provide separately from device 710 until connection of shaft 714 to end-effector assembly 716, or may be disposed on clevis 734 of end-effector assembly 716 prior to connection. Securing member 718 may include cut out sections laser cut into securing member 718. The cut out sections may have any size and/or shape, and may enhance the flexibility and/or grip of securing member 718.

Securing member 718 may have a proximal end 756 and a distal end 758. Proximal end 756 of securing member 718 may be located closer to the distal portion 722 than a proximal end 720 of shaft 714. Distal end 758 of securing member 718 may include a retainer 760 having a recess 761 configured to receive protrusion 762 on proximal portion 740 of clevis 734. In other embodiments, securing member 718 may include a protrusion to be received by a recess on an exterior surface of proximal portion 740 of clevis 734. Various other coupling mechanisms are also contemplated such as, for example, an external cuff or tab to lock securing member 718 relative to proximal portion of clevis 734.

Referring to FIGS. 5A and 5B, medical device 710 may be assembled by aligning proximal portion 740 of clevis 734 with distal portion 722 of shaft 714. In particular, the half-cylindrical portions (i.e., proximal portion 740 and distal portion 722) may be flush mounted together to form a substantially cylindrical joint 764. In this configuration, second fitting 732 may be aligned with first fitting 730 of elongate member 726 so that groove 732a of second fitting may receive enlargement 730b of first fitting 730 and enlargement 732b of second fitting 732 may be received in groove 730a of first fitting 730. In some embodiments, there may be some flexibility between the shapes of first fitting 730 and second fitting 732 to allow friction fit or some deformation when first fitting 730 is aligned and coupled to second fitting 732.

Figures 26A, 26B:
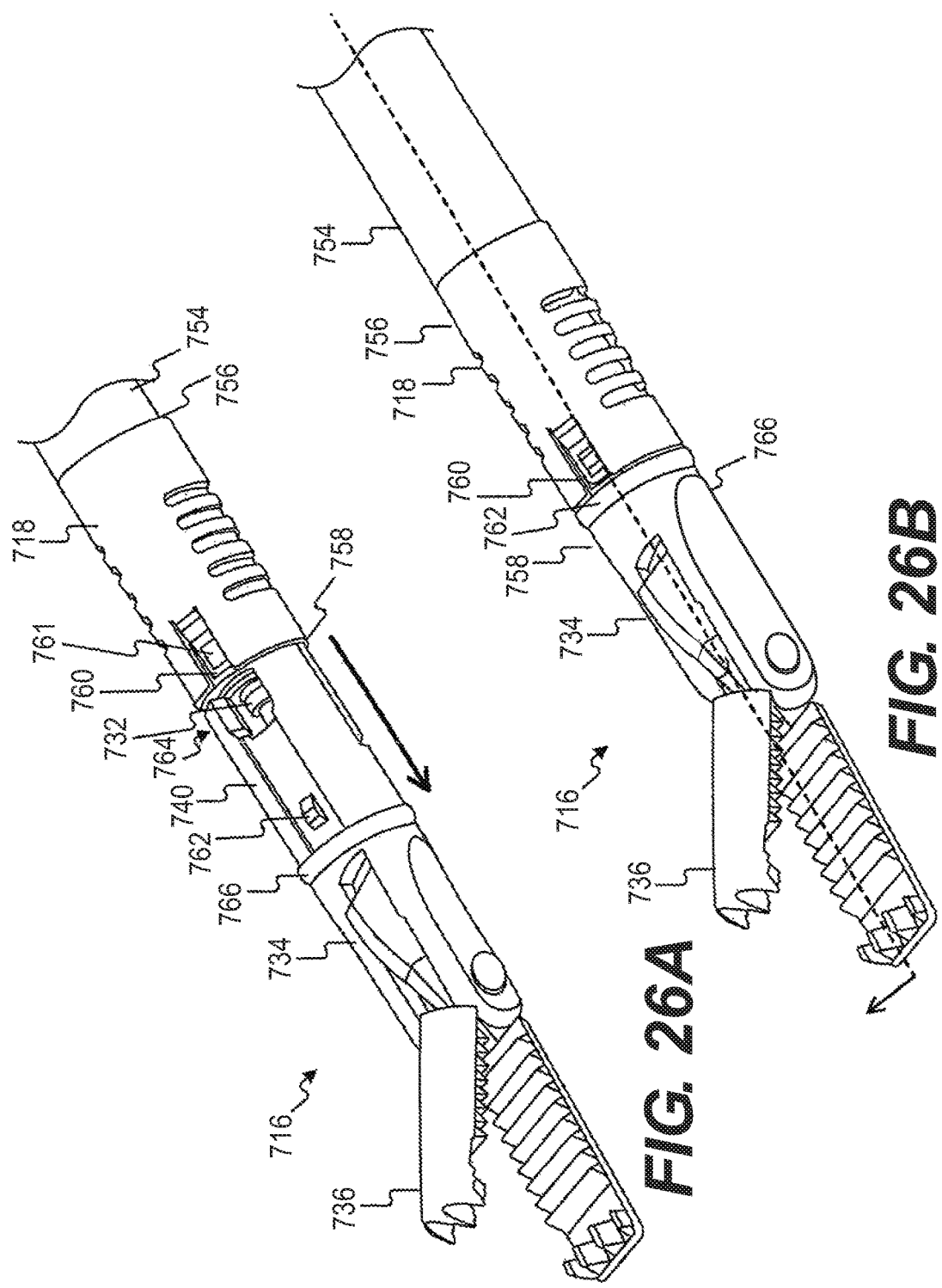
FIG. 26A is a partial perspective view of the medical device of FIG. 22 with the securing member in a first position, according to an exemplary embodiment of the disclosure.
FIG. 26B is a partial perspective view of the medical device of FIG. 22 with the securing member in a second position, according to an exemplary embodiment of the disclosure.

Securing member 718 may move distally relative to distal portion 722 of shaft 714 and end effector assembly 716 when proximal portion 740 of clevis 734 and distal portion 722 of shaft 714 are aligned to form substantially cylindrical joint 764. In particular, securing member 718 may slide distally from a first position as shown in FIG. 26A to a second position as shown in FIG. 26B. In the first position, securing member 718 may be positioned proximal to distal portion 722 of shaft 714. In the second position, a substantial portion of securing member 718 may be disposed around substantially cylindrical joint 764.

End-effector assembly 716 may remain in a fixed position relative to distal portion 722 of shaft 714 as securing member 718 is moved from the first position to the second position. In some embodiments, a rim 766 may be provided on clevis 734 to limit distal movement of securing member 718 beyond the second position. In some embodiments, a stop (not shown) may also be provided on shaft 714 to limit proximal movement of securing member 718 beyond the first position.

Figure 26C:
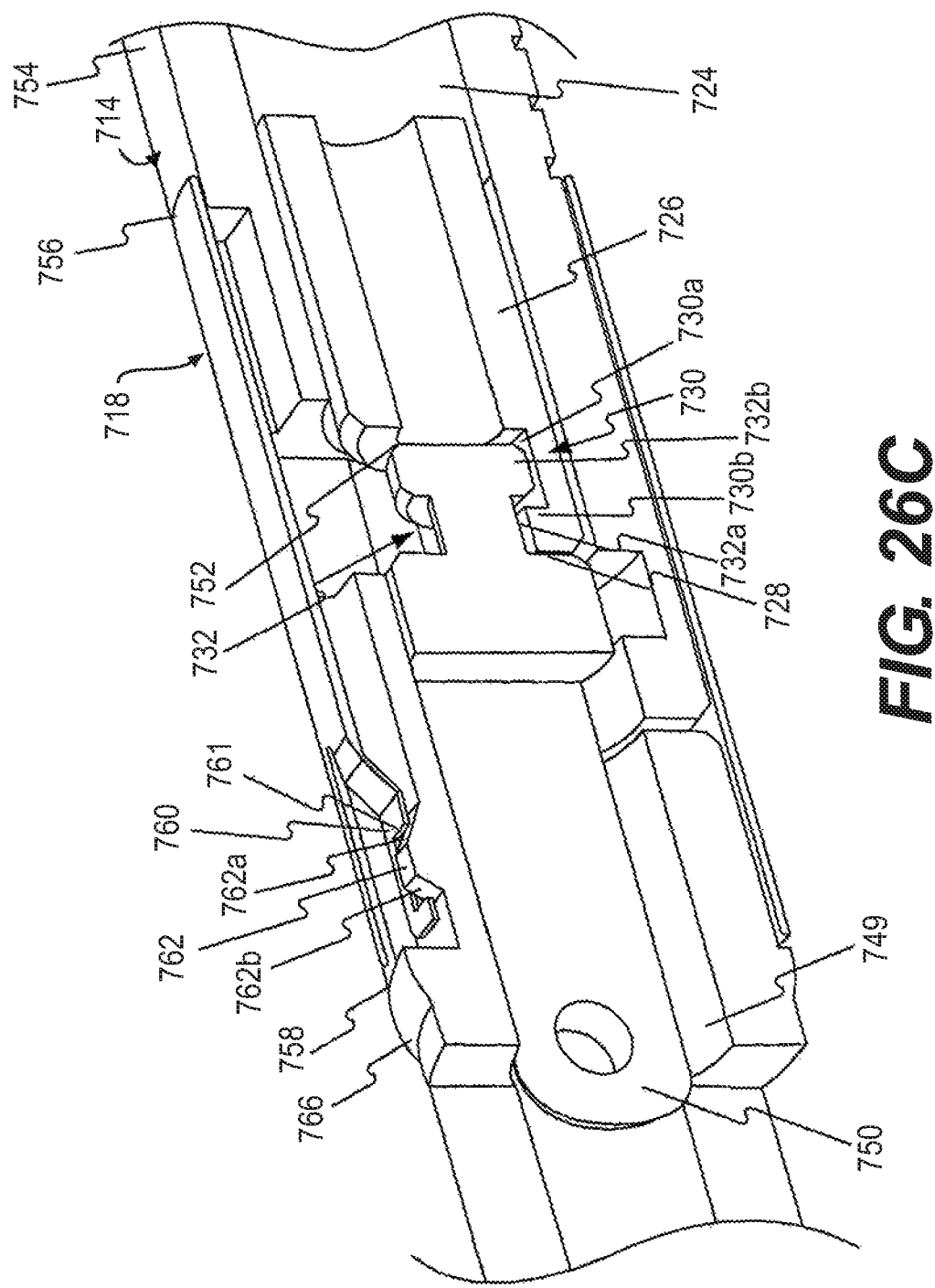
FIG. 26C is a cross-section view of FIG. 26B, according to an exemplary embodiment of the disclosure.

As illustrated in FIG. 26C, when securing member 718 is in the second position, recess 761 of retainer 760 may receive protrusion 762 on proximal portion 740 of clevis 734 to connect end-effector assembly 716 to distal portion 722 of shaft 714. Retainer 760 and protrusion 762 may form a snap-fit connection.

In some embodiments, protrusion 762 may be shaped to facilitate quick connection of retainer 760 and protrusion 762. In particular, protrusion 762 may have a proximally facing surface 762a having a moderate slope to facilitate distal movement of retainer 760 over protrusion 762 so as to connect retainer 760 to protrusion 762. In addition, distally facing surface 762b may have a greater slope than proximally facing surface 762a such that a force required to remove protrusion 762 from recess 761 of retainer 760 is greater than the force required to slide retainer 760 over protrusion 762. In this manner, end-effector assembly 716 may remain connected during use. In some embodiments, surfaces 762a and 762b may have notches to better engage retaining 60. It is contemplated that retainer 760 and protrusion 762 may have a tight friction enhanced fit or, alternatively, may fit together with slight deformation of retainer 760 and protrusion 762 to enhance engagement.

When protrusion 762 is received in recess 761 of retainer 760, a radial force may be exerted on first fitting 730 and second fitting 732 so as to couple first fitting 730 and second fitting 732. A user can then manipulate elongate member 726 at handle portion 712 to move elongate member 726 and actuator 30 relative to lumen 724 of shaft 714 and through-hole 749 of clevis 734, thereby controlling movement, actuation, and/or operation of the pair of end-effectors 736. Additional elements such as spring washers may be provided to bias end-effector assembly 716 against the distal portion 722 of shaft 714 or vice versa to facilitate engagement of end effector assembly 716 to distal portion 722 of shaft 714, take up tolerances, and provide pre-load to ensure a fully engaged and locked assembly.

A user may apply an axial force such as a proximally directed force to securing member 718 to slide securing member 718 from the second position (FIG. 25B) to the first position (FIG. 25A), so as to release protrusion 762 from recess 761 of retainer 760 and disconnect end-effector assembly 716 from distal portion 722 of shaft 714. Other end-effector assemblies (either the same or different types) may then be connected to distal portion 722 of shaft 714.

In another embodiment, securing member 718 may be made of a flexible material that can change cross-sectional shape to disconnect end-effector assembly 716 from distal portion 722. In this embodiment, securing member 718 may have a substantially circular cylindrical cross-sectional shape in the first position. Securing member may be moved distally from the first position to the second position, and retainer 760 may receive protrusion 762 to connect end-effector assembly 716 to distal portion 722.

In order to disconnect end-effector assembly 716 from distal portion 722, a user may squeeze lateral portions of securing member 718 so as to change the shape of securing member 718 from the substantially circular cylindrical cross-sectional shape to a substantially vertical oblong cylindrical cross-sectional shape. By doing so, retainer 760 may release protrusion 762. In this embodiment, securing member 718 may be flexible so as to return to the substantially circular cross-sectional shape. Securing member 718 may then be moved proximally from the second position to the first position. In the first position, end-effector assembly 716 may be removed and other end-effector assemblies (either the same or different types) may be connected to distal portion 722 of shaft 714. It is contemplated that clevis 734 may have scallops to facilitate deformation of securing member 718, and securing member 718 may have dents, taps, or other structures to aid in grasping and squeezing securing member 718.

In yet another embodiment, securing member 718 may be rotated relative to end-effector assembly 716 and distal portion 722 of shaft 714 to couple and/or decouple securing member from shaft 714. Various other types of movements of securing member 718 are also contemplated such as, for example, snapping securing member 718 around substantially cylindrical joint 764, fitting securing member 718 around substantially cylindrical joint 764 with a screw thread, or wrapping securing member 718 around substantially cylindrical joint 764.

Alternative non-limiting examples of end-effector assemblies having various shapes and/or distal configurations are shown in FIGS. 6A and 6B. In the end-effector assembly 716a depicted in FIG. 27A, the pair of end-effectors 736a may be scissors. Scissors may curve to the right or left for use by an right-handed or left-handed operator. In the end-effector assembly 716b depicted in FIG. 27B, the pair of end-effectors 736b may be dissectors. Dissectors 736b may curve to the right or left for use by a right-handed or left-handed operator.

The disclosed medical device may have certain advantages. As noted above, the disclosed medical device 710 may be configured so that multiple end-effector assemblies, having different end-effectors, may be used interchangeably with a single shaft 714 and handle portion 712. This may provide a surgeon with greater capabilities during a procedure. Specifically, surgeons may have the flexibility to create specific devices as needed. Moreover, the various end-effector assemblies may be provided together in kit form. This may be advantageous for hospital inventory control, as the medical device may occupy less space in the operating room and/or storage.

It is also contemplated that in one embodiment, the distal portion of the shaft 714 may include features of the proximal portion of the distal adapter 300 and the articulation links 400, and more proximal portions of the shaft 714 may include the features of the proximal adapter 500 and the instrument shaft section 60. In such an embodiment, articulation control member portions similar to the articulation control member portions 111, 112, 113, and 114 may be used to deflect the distal portion of the shaft 714.

It will be apparent to those skilled in the art that various modifications and variations can be made in the disclosed systems and processes without departing from the scope of the disclosure. Other embodiments of the disclosure will be apparent to those skilled in the art from consideration of the specification and practice of the aspects disclosed herein. It is intended that the specification and examples be considered as exemplary only, with a true scope and spirit of the disclosure being indicated by the following claims.

What is claimed is:

1. An instrument shaft, comprising:
 a proximal section including:
  a distal portion, and
  a wall formed by concentric layers, the concentric layers including a first layer and a second layer, wherein the first layer is an outermost layer of the concentric layers, and the second layer is separated from the first layer by one or more additional layers; and
 a distal section including:
  a proximal portion, wherein the proximal portion of the distal section is coupled to the distal portion of the proximal section, and
  a sheath that directly contacts the first layer and the second layer of the concentric layers to couple the proximal portion of the distal section to the distal portion of the proximal section, wherein the sheath overlaps with at least one of the first layer and the second layer along a radial direction of the instrument shaft.

2. The instrument shaft of claim 1, wherein the first layer includes a distalmost end face, the sheath includes a proximalmost end face, and the distalmost end face directly contacts the proximalmost end face.

3. The instrument shaft of claim 2, wherein a radially-inner surface of the sheath directly contacts a radially-outer surface of the second layer.

4. The instrument shaft of claim 1, wherein a radially-outer surface of the sheath directly contacts a radially-inner surface of the first layer and a radially-outer surface of the second layer.

5. The instrument shaft of claim 1, wherein a radially-outer surface of the sheath directly contacts a radially-inner surface of the first layer.

6. The instrument shaft of claim 5, wherein a radially-inner surface of the sheath contacts a radially-outer surface of the second layer.

\* \* \* \* \*